US009615583B2

(12) United States Patent
Kloepper et al.

(10) Patent No.: US 9,615,583 B2
(45) Date of Patent: *Apr. 11, 2017

(54) **INOCULANTS INCLUDING *BACILLUS* BACTERIA FOR INDUCING PRODUCTION OF VOLATILE ORGANIC COMPOUNDS IN PLANTS**

(71) Applicant: Auburn University, Auburn, AL (US)

(72) Inventors: Joseph W. Kloepper, Auburn, AL (US); Henry Y. Fadamiro, Auburn, AL (US); Esther N. Ngumbi, Ukunda (KE); Kate W. Nangle, Waltham, MA (US)

(73) Assignee: Auburn University, Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,397

(22) Filed: Feb. 3, 2016

(65) Prior Publication Data

US 2016/0192661 A1     Jul. 7, 2016

Related U.S. Application Data

(62) Division of application No. 13/871,423, filed on Apr. 26, 2013, now Pat. No. 9,282,745, which is a division of application No. 13/323,379, filed on Dec. 12, 2011, now Pat. No. 8,445,255.

(60) Provisional application No. 61/421,979, filed on Dec. 10, 2010.

(51) Int. Cl.
| | |
|---|---|
| *A01N 63/00* | (2006.01) |
| *C12N 1/20* | (2006.01) |
| *C12R 1/07* | (2006.01) |

(52) U.S. Cl.
CPC ............... *A01N 63/00* (2013.01); *C12N 1/20* (2013.01); *C12R 1/07* (2013.01)

(58) Field of Classification Search
None
See application file for complete search history.

(56) References Cited

U.S. PATENT DOCUMENTS

| 6,524,998 B1 | 2/2003 | Kloepper et al. |
| 8,445,255 B2 | 5/2013 | Kloepper et al. |
| 2008/0152684 A1* | 6/2008 | Tzeng ............... A01N 63/00 424/405 |

FOREIGN PATENT DOCUMENTS

| CN | 1244771 | 2/2000 |
| CN | 1766091 | 5/2006 |
| WO | 0051435 | 9/2000 |

OTHER PUBLICATIONS

Backman et al., "Bacteria for Biological Control of Plant Diseases", Environmentally Safe Approaches to Crop Disease Control, CRC Press, 1997, 95-109.
Boutard-Hunt et al., "Impact of Plant Growth-Promoting Rhizobacteria and Natural Enemies on Myzus persicae (Hemiptera: Aphididae) Infestations in Pepper", Journal of Economic Entomology, 2009, 102(6): 2183-2191.
Cardoza et al., In Vivo Volatile Emissions from Peanut Plants Induced by Simultaneous Fungal Infection and Insect Damage, Journal of Chemical Ecology, Jan. 2002, 28(1):161-174.
Chen et al., "Differential Electroantennogram Response of Females and Males of Two Parasitoid Species to Host-Related Green Leaf Volatiles and Inducible Compounds", Bulletin of Entomological Research, 2007, 97:515-522.
Cleyet-Marel et al., "Plant Growth Enhancement by Rhizobacteria", 2001, 40:911-915.
Farmer et al., "Jasmonates and Related Oxylipins in Plant Responses to Pathogenesis and Herbivory", Current opinion in Plant Biology, 2003, 6:372-378.
Glick, "The Enhancement of Plant Growth by Free-Living Bacteria", Can. J. Microbiol., 1995, 41:109-117.
Hanafi et al., Induced Resistance of Tomato to Whiteflies and Pythium with the PGPR Bacillus subtilis in a Soilless Crop Grown under Greenhouse Conditions, Acta Hort., 2007, 747:315.
Humberto et al., "Inoculation of Tomato Plants (*Solanum lycopersicum*) with Growth-Promoting Bacillus Subtilis Retards Whitefly *Bemisia tabaci* Development", Planta, 2010, 231:397-410.
Jalali et al., "Studies on Host Age Preference and Biology of Exotic Parasite, Cotesia Marginiventris (Cresson) (Hymenoptera: Braconidae)", Entomon, 1987, 12(1):59-62.
King et al., "A High Indicence of Parasitism of *Heliothis* SSP. [LEP: Noctuidae] Larvae in Cotton in Southeastern Arkansas", Entomophaga, 1985, 30(4):419-426.
Kloepper et al., "Bacterial Endophytes as Elicitors of Induced Systemic Resistance", Soil Biology, 2006, 9:33-51.
Kloepper, "Plant Growth-Promoting Rhizobacteria as Biological Control Agents", Soil Microbial Ecology, 1992, 9:255-274.
Kokalis-Burelle et al., Plant Growth-Promoting Rhizobacteria as transplant Amendments and their Effects on Indigenous Rhizosphere Microorganisms, Applied Soil Ecology, 2006, 31:91-100.
Lewis et al., "Rearing Microplitis Croceipes in the Laboratory with Heliothis Sea as Host", Journal of Economic Entomology, 1970, 63:657-658.
Lucy et al., "Applications of Free Living Plant Growth-Promoting Rhizobacteria", Antonie van Leeuwenhoek, 2004, 86:1-25.
Mithofer et al., "Biotic and Heavy Metal Stress Response in Plants: Evidence for Common Signals", Federation of European Biochemical Societies, 2004, 566:1-5.
Ngumbi et al., "Comparative GC-EAD Responses of a Specialist (Microplitis Croceipes) and a Generalist (Cotesi Marginiventris) Parasitoid to Cotton Volatiles Induced by Two Caterpillar Species", J. Chem. Ecol., 2009, 35:1009-1020.

(Continued)

*Primary Examiner* — Oluwatosin Ogunbiyi
(74) *Attorney, Agent, or Firm* — Andrus Intellectual Property Law, LLP

(57) ABSTRACT

Disclosed are inoculants that include *Bacillus* bacteria and induce production of volatile organic compounds (VOCs) by a plant that has been treated with the inoculant.

16 Claims, 10 Drawing Sheets

(56) References Cited

OTHER PUBLICATIONS

Preston et al., "Tobacco Mosaic Virus Inoculation Inhibits Wound-Induced Jasmonic Acid-Mediated Responses within but not Between Plants", Planta, 1999, 209:87-95.
Ramamoorthy et al., "Induction of Systemic Resistance by Plant Growth Promoting Rhizobacteria in Crop Plants Against Pests and Diseases", Crop Protection, 2001, 20:1-11.
Rose et al., "Specificity of Systemically Released Cotton Volatiles as Attractants for Specialist and Generalist Parasitic Wasps", Journal of Chemical Ecology, 1998, 24(2):303.
Ryu et al., "Bacterial Volatiles Induce Systemic Resistance in Arabidopsis", Plant Physiology, Mar. 2004, 134:1017-1026.
Shorey et al., "Mass-Rearing of the Larvae of Nine Noctuid Species on a Simple Artificial Medium", Journal of Economic Entomology, 1965, 58:522-524.
Stadelbacher et al., "Parasitism of Heliothis Zea and H. Virescens (Lepidoptera: Noctuidae) Larvae in Wild and Cultivated Host Plants in the Delta of Mississippi", Environmental Entomology, 1984, 13:1166-1167.
Takabayashi et al., "Volatile Herbivore-Induced Terpenoids in Plant-Mite Interactions: Variation Caused by Biotic and Abiotic Factors", Journal of Chemical Ecology, 1994, 20(6):1328-1329.
Van Loon et al., "Systemic Resistance Induced by Rhizosphere Bacteria", Annu. Rev. Phytopathol, 1998, 36:453-83.
Zehnder et al., "Insect Feeding on Cucumber Mediated by Rhizobacteria-Induced Plant Resistance", Entomologia Experimentalis et Applicata, 1997, 83:81-85.
Alborn et al., "An Elicitor of Plant Volatiles from Beet Armyworm", Science, 1997, 276:945.
Ament et al., "Jasmonic Acid Is a Key Regulator of Spider Mite-Induced Volatile Terpenoid and Methyl Salicylate Emission in Tomato", Plant Physiology, Aug. 2004, 135:2025-2037.
Banchio et al., "Soil Bacteria Elevate Essential Oil Accumulation and Emissions in Sweet Basil", J. Agric. Food Chem., 2009, 57:653-657.
Bashan, "Inoculants of Plant Growth-Promoting Bacteria for Use in Agriculture", Biotechnology Advances, 1998, 16(4):729-770.
Burkett-Cadena et al., "Suppressiveness of root-knot nematodes mediated by rhizobacteria", Biological Control, 2008, 47:55-59.
Bruxelles et al., "Signals Regulating Multiple Responses to Wounding and Herbivores", Critical Reviews in Plant Sciences, 2001, 20(5):487-521.
Chen et al., Nature Biotechnology, Sep. 2007, 25(9):1007-1014.
De Moraes et al., "Herbivore-infested plants selectively attract parasitoids", Nature, Jun. 11, 1998, 393:570.
Engelberth et al., "Airborne signals prime plants against insect herbivore attach", PNAS, Feb. 10, 2004, 101(6):1781-1785.
Gouinguene et al., "Antennal electrophysiological responses of three parasitic wasps to caterpillar-induced volatiles from maize, (*Zeas mays mays*), cotton (*Gossypium herbaceum*), and cowpea (*Vigna unguiculata*)", Journal of chemical Ecology, May 2005, 31(5)1023.
Couinguene et al., "The effects of abiotic factors on induced volatile emissions in corn plants", Plant Physiology, Jul. 2002, 129:1296-1307.
Hassan et al., Biocontrol, 2010, 55:531-542.
Ji et al., "Integrated biological control of bacterial speck and spot of tomato under field conditions using foliar biological control agents and plant growth-promoting rhizobacteria", Biological Control, 2006, 36:358-367.
Kessler et al., "Defensive function of herbivore-induced plant volatile emissions in nature", Science, 2001, 291:2141.

Kloepper et al., "Plant root-bacterial interactions in biolobigal control of soilborne diseases and potential extension to systemic and foliar diseases", Australasian Plant Pathology, 1999, 28:21-26.
Kloepper et al, "Induced systemic resistance and promotion of plant growth by *Bacillus* spp.", The American Phytopathological Society Symposium: The Nature of Application of Biocontrol Microbes: *Bacillus* spp., 2004, 94(11):1259.
Kokalis-Burelle et al., "Amendment of muskmelon and watermelon transplant media with plant growth-promoting rhizobacteria: effects on seedling quality, disease, and nematode resistance", Hort Technology, Jul.-Sep. 2003, 13(3):476.
Kumar et al., International Journal of Applied Biology and Pharmaceutical Technology, Jan.-Mar. 2011, 2:488-495.
Loughrin et al., "Diurnal cycle of emission of induced volatile terpenoids by herbivore-injured cotton plants", Proc. Natl. Acad. Sci. USA, Plant Biology, Dec. 1994, 91:11836-11840.
Mattiacci et al., "Beta-glucosidase: an elicitor of herbivore-induced plant odor that attracts host-searching parasitic wasps", Proc. Natl. Acad. Scie. USA, Plant Biology, Mar. 1995, 92:2036-2040.
Mithofer et al., "Effects of feeding spodoptera littoralis on lima beam leaves. II. Continuous mechanical wounding resembling insect feeding is sufficient to elicit herbivory-related volatile emission", Plant Physiology, Mar. 2005, 137:1160-1168.
Pieterse et al., "Systemic resistance in arabidopsis induced by biocontrol bacteria is independent of salicyclic acid accumulation and pathogenesis-related gene expression", The Plant Cell, Aug. 1996, 8:1225-1237.
Raj et al., "Comparative performance of formulations of plant growth promoting rhizobacteria in growth promotion and suppression of downy mildew in pearl millet", Crop Protection, 2003, 22:579-588.
Raupach et al., "Mixtures of plant growth-promoting rhizobacteria enhance biological control of multiple cucumber pathogens", Phytopathology, Jan. 1, 1998, 88(11):1158-1164.
Ryu et al., "Bacterial volatiles promote growth in arabidopsis", PNAS, Apr. 15, 2003, 100(8):4927-4932.
Schippers et al., "Interactions of deleterious and beneficial rhizosphere microorganisms and the effect of cropping practices", Ann. Rev. Phytopathol., 1987, 25:339-358.
Tamura et al., "MEGA4: Molecular Evolutionary Genetics Analysis (MEGA) Software Version 4.0", Mol. Biol. Evol. 2007, 24(8):1596-1599.
Tatusova et al., "Blast 2 Sequences, a new tool for comparing protein and nucleotide sequences", FEMS Microbiology Letters, 1999, 174:247-250.
Thaler et al., "Cross-talk between jasmonate and salicylate plant defense pathways: effects on several plant parasites", Oecologia, 2002, 131:227-235.
Yildirim et al., "Ameliorative effects of biological treatments on growth of squash plants under salt stress", Scientia Horticulturae, 2006, 111:1-6.
Zahnder et al., "Application of rhizobacteria for induced resistance", European Journal of Plant Pathology, 2001, 107:39-50.
Ph.D. Dissertation of Ramirez, "Exploring the relation between plant phosphorus nutrition and growth promotion by bacillus subtilis/amyloliquefaciens strains," Auburn University, Aug. 2, 2010.
Office Action issued Nov. 27, 2012, in connection with Panamanian Patent Application No. 85525.
International Search Report for PCT/US2011/064403 dated Feb. 17, 2012.
Written Opinion for PCT/US2011/064403 dated Feb. 17, 2012.
International Preliminary Report on Patentability for PCT/US2011/064403 dated Jun. 20, 2011.
Office Action and Search Report for CN201180066750.3 dated Feb. 4, 2015.
GenBank Accession #HQ021420, Dec. 1, 2011.
Abstract for Lee et al., "Antimicrobial fibers from mixed solutions of cellulose and m-aramid polymers", Abstracts of Papers, 2006.

* cited by examiner (A)

(B)

INOCULANTS INCLUDING *BACILLUS* BACTERIA FOR INDUCING PRODUCTION OF VOLATILE ORGANIC COMPOUNDS IN PLANTS

CROSS-REFERENCE TO RELATED APPLICATIONS

The present application is a divisional of U.S. patent application Ser. No. 13/871,423, filed Apr. 26, 2013, which application was published on Oct. 10, 2013, as US2013/0267418, and which issued on Mar. 15, 2016, as U.S. Pat. No. 9,282,745, which application is a divisional of U.S. patent application Ser. No. 13/323,379, filed Dec. 12, 2011, which application was published on Jun. 14, 2012, as US2012/0149571, and which issued on May 21, 2013, as U.S. Pat. No. 8,445,255, and which claims the benefit of priority under 35 U.S.C. §119(e) to U.S. provisional application Ser. No. 61/421,979, filed on Dec. 10, 2010, the contents of which are incorporated herein by reference in their entirety.

FIELD

The present subject matter relates to the field of plant growth-promoting rhizobacteria (PGPR). In particular, the present subject matter relates to PGPR that induce production of volatile organic compounds by plants that have been treated with the bacteria.

BACKGROUND

The induction of volatile organic compounds (VOCs) in plants has gone virtually unexamined, despite evidence that induction of plant volatiles is dependent on the interactions of biotic factors, such as plant hormones (de Bruxelles and Roberts, 2001; Ament et al., 2004), herbivore-derived elicitors (Spiteller and Boland 2003), and associated microorganisms including pathogens (Preston et al., 1999; Cardoza et al., 2002), as well as abiotic factors, such as wounding (Mithofer et al., 2005), heavy metals (Mithofer et al., 2004), and temperature and light (Takabayashi et al., 1994). Plant growth promoting rhizobacteria (PGPR) represent a wide range of root-colonizing bacteria whose application often is associated with increased rates of plant growth (Kloepper, 1992; Zehnder et al., 1997), suppression of soil pathogens (Schippers et al., 1987), and the induction of systemic resistance against insect pests (Kloepper et al., 1999; Ryu et al., 2004). The lack of research on induction of VOCs in plants and whether PGPR can influence production of VOCs in plants is surprising given that PGPR are increasingly being applied in the production of several field crops in some parts of the world (Backman et al., 1997; Cleyet-Marcel et al., 2001). Backman et al. (1997) reported that 60-75% of the US cotton crop is treated with the PGPR product Kodiak®, a *Bacillus subtilis* product used for suppression of *Fusarium* and *Rhizoctonia* soil pathogens. Here, the potential effects of PGPR on induction of cotton volatiles and consequences for attraction cotton herbivores and their parasitoids were studied. Surprisingly, PGPR were observed to elicit changes in plant VOC's with important ramifications. Knowledge of the effects of PGPR on the induction of plant volatiles and insect-plant interactions will likely contribute to the increased adoption of PGPR products and development of better products and also mitigate against potential negative impacts of these products.

SUMMARY

Disclosed are isolated plant growth promoting rhizobacteria (PGPR) and inoculants thereof that induce production of one or more volatile organic compounds (VOCs) by a plant that has been treated with the PGPR. Suitable PGPR may include *Bacillus* species.

The VOCs produced by the plant may include, but are not limited to, compounds selected from alpha-pinene, beta-pinene, beta-myrcene, cis-3-hexenyl acetate, limonene, beta-ocimene, linalool, (E)-4,8-dimethyl-1,3,7-nonatriene, methyl salicylate, decanal, cis-jasmone, caryophyllene, alpha-humulene, beta-farnesene, and mixtures thereof. The VOCs produced by the PGPR-treated plants preferably modify the behavior of insects exposed to the VOCs. In some embodiments, the insect is an herbivore and the VOCs reduce egg-laying or feeding of the insect on the plant. In further embodiments, the insect is a predator or parasitoid and the VOCs attract the predator or parasitoid to the plant.

The PGPR may be a single strain, species, or genus of bacteria or may comprise a mixture of bacterial strains, species, or genera. For example, the PGPR may be selected from genera including, but not limited to, *Actinobacter, Alcaligenes, Bacillus, Burkholderia, Buttiauxella, Enterobacter, Klebsiella, Kluyvera, Pseudomonas, Rahnella, Ralstonia, Rhizobium, Serratia, Stenotrophomonas, Paenibacillus,* and *Lysinibacillus*.

The PGPR may include *Bacillus* bacteria. The *Bacillus* bacteria may have a comprise a 16S rDNA nucleic acid sequence comprising SEQ ID NO:1, SEQ ID NO:2, SEQ ID NO:3, or SEQ ID NO:4 or may comprise a 16S rDNA nucleic acid sequence having at least 90%, 91%, 92%, 93%, 94%, 95%, 96%, 97%, 98%, or 99% sequence identity to one or more of SEQ ID NO:1, SEQ ID NO:2, SEQ ID NO:3, SEQ ID NO:4, and SEQ ID NO:5. Specific *Bacillus* bacteria may include *Bacillus amyloliquefaciens* (e.g. *Bacillus amyloliquefaciens* strain AP-136, deposited with the United States Department of Agriculture on Dec. 2, 2011, under Accession No. NRRL B-50614; *Bacillus amyloliquefaciens* strain AP-188, deposited with the United States Department of Agriculture on Dec. 2, 2011, under Accession No. NRRL B-50615; *Bacillus amyloliquefaciens* strain AP-218, deposited with the United States Department of Agriculture on Dec. 2, 2011, under Accession No. NRRL B-50618; *Bacillus amyloliquefaciens* strain AP-219, deposited with the United States Department of Agriculture on Dec. 2, 2011, under Accession No. NRRL B-50619; and *Bacillus amyloliquefaciens* strain AP-295, deposited with the United States Department of Agriculture on Dec. 2, 2011, under Accession No. NRRL B-50620); *Bacillus mojavensis* (e.g. *Bacillus mojavensis* strain AP-209, deposited with the United States Department of Agriculture on Dec. 2, 2011, under Accession No. NRRL B-50616); *Bacillus solisalsi* (e.g., *Bacillus solisalsi* strain AP-217, deposited with the United States Department of Agriculture on Dec. 2, 2011, under Accession No. NRRL B-50617); *Bacillus pumilus* (e.g., *Bacillus pumilus* strain INR-7 (otherwise referred to as BU F-22, deposited with the United States Department of Agriculture on Jul. 23, 2008, under Accession No. NRRL B-50153; and BU-F33, deposited with the United States Department of Agriculture on Oct. 15, 2008, under Accession No. NRRL B-50185)); *Bacillus simplex* (e.g., *Bacillus simplex* strain ABU 288, deposited with the United States Department of Agriculture on Feb. 18, 2010, under Accession No. NRRL B-50340); and *Bacillus subtilis* (*Bacillus subtilis* strain MBI 600), deposited with the United States Department of Agriculture on Nov. 14, 2011, under Accession No. NRRL B-50595), and mixtures or blends thereof.

Also disclosed are inoculants that include the presently disclosed PGPR and optionally a carrier. The inoculants may comprise additional active ingredients such as phytohormones (e.g., acetoin, 2,3-butanediol, and indole-acetic acid) and anti-microbial compounds (e.g., phenylethanol and 4-hydroxybenzoate).

The disclosed PGPR and inoculants thereof may be utilized in methods for modifying insect behavior towards a plant. In some embodiments the methods include administering an inoculant comprising the PGPR to a plant, to seeds, tubers, or rhizomes of a plant, or to soil or the environment surrounding a plant. The method may result in reducing egg-laying or feeding of an herbivore on the plant and/or may result in attracting predators or parasitoids to the plant. Suitable plants for the methods may include, but are not limited to alfalfa, rice, barley, rye, cotton, sunflower, peanut, corn, potato, sweet potato, bean, pea, lentil chicory, lettuce, endive, cabbage, brussel sprout, beet, parsnip, turnip, cauliflower, broccoli, turnip, radish, spinach, onion, garlic, eggplant pepper, celery, carrot, squash, pumpkin, zucchini, cucumber, apple, pear, melon, citrus, strawberry, grape, raspberry, pineapple, soybean, canola, oil seed rape, spring wheat, winter wheat, tobacco, tomato, sorghum, and sugarcane.

DETAILED DESCRIPTION

Figure 1:
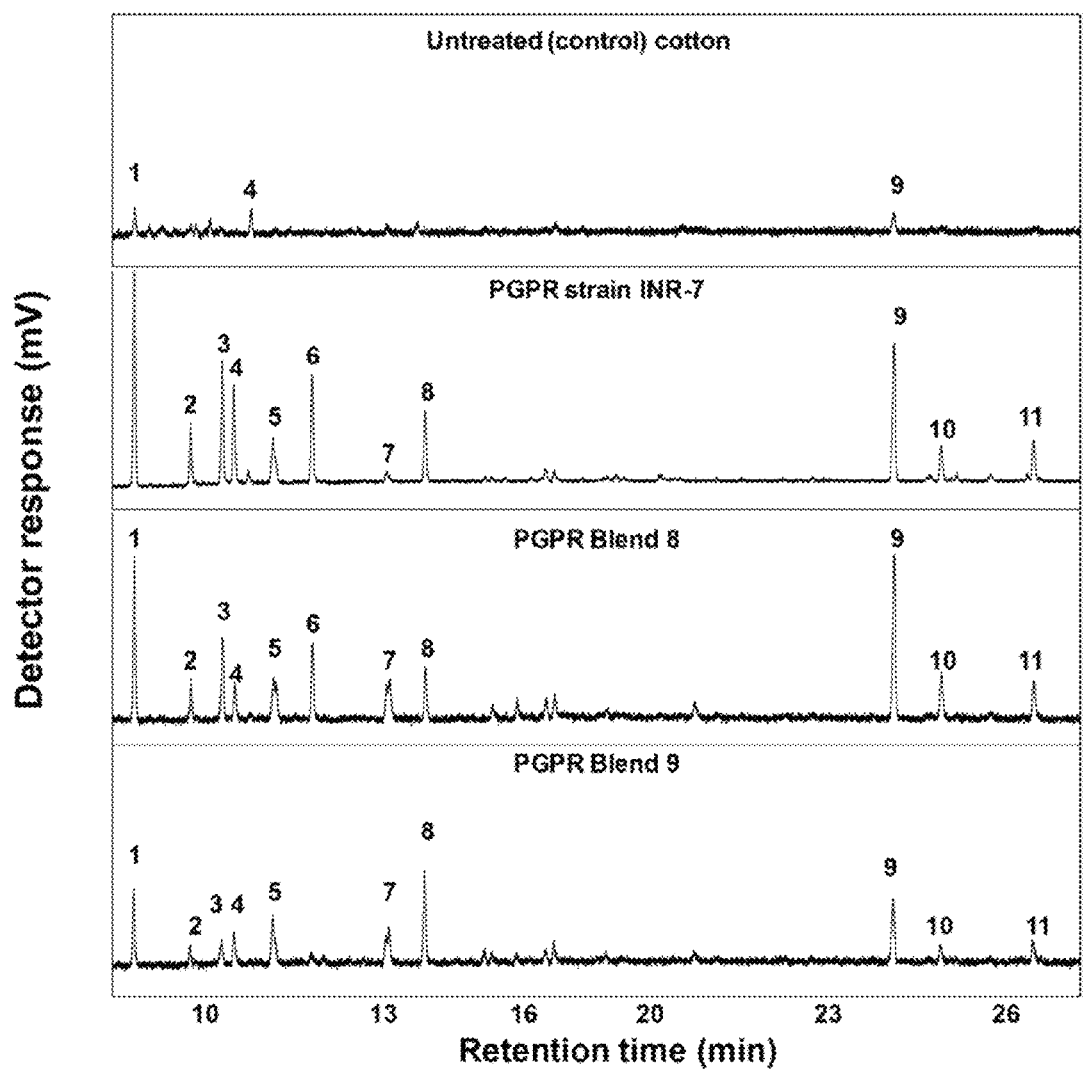
FIG. 1. Chromatographic profiles of headspace volatiles from untreated (control) cotton plants vs. cotton plants treated with PGPR strain INR-7, PGPR Blend 8, or PGPR Blend 9. Identified compounds: (1) α-pinene; (2) β-pinene; (3) β-myrcene; (4) cis-3-hexenyl acetate; (5) Limonene; (6) β-ocimene; (7) linalool; (8) unknown; (9) caryophyllene; (10) α-humulene; (11) β-farnesene FIG. 2. Chromatographic profiles of headspace volatiles collected from untreated (control 1) cotton plants uninfested with caterpillars, untreated (control 2) cotton plants infested with caterpillars, PGPR Blend 9 treated cotton plants uninfested with caterpillars, and PGPR Blend 9 treated cotton plants infested with caterpillars. Identified compounds: (1) cis-3-hexenal; (2) trans-2-hexenal; (3) cis-3-hexen-1-ol; (4) trans-2-hexen-1-ol; (5) α-pinene; (6) β-pinene; (7) myrcene; (8) cis-3-hexenyl acetate; (9) trans-2-hexenyl acetate; (10) limonene; (11) β-ocimene; (12) linalool; (13) unknown; (14) (E)-4,8-dimethyl-1,3,7-nonatriene; (15) cis-3-hexenyl butyrate; (16) trans-2-hexenyl butyrate; (17) n-decanal (18) cis-3-hexenyl-2-methyl butyrate; (19) trans-2-hexenyl-2-methyl butyrate; (20) indole; (21) isobutyl tiglate; (22) (E)-2-hexenyl tiglate; (23) cis-jasmone; (24) caryophyllene; (25) α-trans bergamotene; (26) α-farnesene; (27) α-humulene; (28) β-farnesene.

The disclosed subject matter is further described below.

Unless otherwise specified or indicated by context, the terms "a", "an", and "the" mean "one or more." For example, "a peptide" should be interpreted to mean "one or more peptides" unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

The term "plant" as utilized herein should be interpreted broadly and may include angiosperms and gymnosperms, dicots and monocots, and trees. Examples of angiosperm dicots may include, but are not limited to tomato, tobacco, cotton, rapeseed, field beans, soybeans, peppers, lettuce, peas, alfalfa, clover, cabbage, broccoli, cauliflower, brussel sprouts), radish, carrot, beets, eggplant, spinach, cucumber, squash, melons, cantaloupe, and sunflowers. Example of angiosperm monocots may include, but are not limited to asparagus, field and sweet corn, barley, wheat, rice, sorghum, onion, pearl millet, rye, oats, and sugar cane. Woody plants may include, but are not limited to fruit trees, acacia, alder, aspen, beech, birch, sweet gum, sycamore, poplar, willow, fir, pine, spruce, larch, cedar, and hemlock.

The term "plant growth promoting rhizobacteria" or "PGPR" refers to a group of bacteria that colonize plant roots, and in doing so, promote plant growth and/or reduce disease or damage from predators. Bacteria that are PGPR may belong to genera including, but not limited to *Actinobacter, Alcaligenes, Bacillus, Burkholderia, Buttiauxella, Enterobacter, Klebsiella, Kluyvera, Pseudomonas, Rahnella, Ralstonia, Rhizobium, Serratia, Stenotrophomonas, Paenibacillus*, and *Lysinibacillus*.

The term "volatile organic compound" or "VOC" refers to an organic compound that normally is gaseous under ambient conditions. As used herein, VOCs may include, but are not limited to of alpha-pinene, beta-pinene, beta-myrcene, cis-3-hexenyl acetate, limonene, beta-ocimene, linalool, (E)-4,8-dimethyl-1,3,7-nonatriene, methyl salicylate, decanal, cis-jasmone, caryophyllene, alpha-humulene, beta-farnesene, and mixtures thereof. As disclosed herein, PGPR have been identified which induce plants to emit VOCs.

The presently disclosed PGPR may be formulated as an inoculant for a plant. The term "inoculant" means a preparation that includes an isolated culture of a PGPR and optionally a carrier, which may include a biologically acceptable medium.

The presently disclosed PGPR may be isolated or substantially purified. The terms "isolated" or "substantially purified" refers to PGPR that have been removed from a natural environment and have been isolated or separated, and are at least 60% free, preferably at least 75% free, and more preferably at least 90% free, even more preferably at least 95% free, and most preferably at least 100% free from other components with which they were naturally associated. An "isolated culture" refers to a culture of the PGPR that does not include significant amounts of other materials such as other materials which normally are found in soil in which the PGPR grows and/or from which the PGPR normally may be obtained. An "isolated culture" may be a culture that does not include any other biological, microorganism, and/or bacterial species in quantities sufficient to interfere with the replication of the "isolated culture." Isolated cultures of PGPR may be combined to prepare a mixed culture of PGPR.

The genus *Bacillus* as used herein refers to a genus of Gram-positive, rod-shaped bacteria which are members of the division Firmicutes. Under stressful environmental conditions, the *Bacillus* bacteria produce oval endospores that can stay dormant for extended periods. *Bacillus* bacteria may be characterized and identified based on the nucleotide sequence of their 16S rRNA or a fragment thereof (e.g., approximately a 1000 nt, 1100 nt, 1200 nt, 1300 nt, 1400 nt, or 1500 nt fragment of 16S rRNA or rDNA nucleotide sequence). *Bacillus* bacteria may include, but are not limited to *B. acidiceler, B. acidicola, B. acidiproducens, B. aeolius, B. aerius, B. aerophilus, B. agaradhaerens, B. aidingensis, B. akibai, B. alcalophilus, B. algicola, B. alkalinitrilicus, B. alkalisediminis, B. alkalitelluris, B. altitudinis, B. alveayuensis, B. amyloliquefaciens, B. anthracis, B. aquimaris, B. arsenicus, B. aryabhattai, B. asahii, B. atrophaeus, B. aurantiacus, B. azotoformans, B. badius, B. barbaricus, B. bataviensis, B. beijingensis, B. benzoevorans, B. beveridgei, B. bogoriensis, B. boroniphilus, B. butanolivorans, B. canaveralius, B. carboniphilus, B. cecembensis, B. cellulosilyticus, B. cereus, B. chagannorensis, B. chungangensis, B. cibi, B. circulans, B. clarkii, B. clausii, B. coagulans, B. coahuilensis, B. cohnii, B. decisifrondis, B. decolorationis, B. drentensis, B. farraginis, B. fastidiosus, B. firmus, B. flexus, B. foraminis, B. fordii, B. foris, B. fumarioli, B. funiculus, B. galactosidilyticus, B. galliciensis, B. gelatini, B. gibsonii, B. ginsengi, B. ginsengihumi, B. graminis, B. halmapalus, B. halochares, B. halodurans, B. hemicellulosilyticus, B. herbertsteinensis, B. horikoshi, B. horneckiae, B. horti, B. humi, B. hwajinpoensis, B. idriensis, B. indicus, B. infantis, B. infernus, B. isabeliae, B. isronensis, B. jeotgali, B. koreensis, B. korlensis, B. kribbensis, B. krulwichiae, B. lehensis, B. lentus, B. licheniformis, B. litoralis, B. locisalis, B. luciferensis, B. luteolus, B. macauensis, B. macyae, B. mannanilyticus, B. mariflavi, B. marmarensis, B. massiliensis, B. megaterium, B. methanolicus, B. methylotrophicus, B. mojavensis, B. muralis, B. murimartini, B. mycoides, B. nanhaiensvis, B. nanhaiisediminis, B. nealsonii, B. neizhouensis, B. niabensis, B. niacini, B. novalis, B. oceanisediminis, B. odysseyi, B. okhensis, B. okuhidensis, B. oleronius, B. oshimensis, B. panaciterrae, B. patagoniensis, B. persepolensis, B. plakortidis, B. pocheonensis, B. polygoni, B. pseudoalcaliphilus, B. pseudofirmus, B. pseudomycoides, B. psychrosaccharolyticus, B. pumilus, B. qingdaonensis, B. rigui, B. ruris, B. safensis, B. salarius, B. saliphilus, B. schlegelii, B. selenatarsenatis, B. selenitireducens, B. seohaeanensis, B. shackletonii, B. siamensis, B. simplex, B. siralis, B. smithii, B. soli, B. solisalsi, B. sonorensis, B. sporothermodurans, B. stratosphericus, B. subterraneus, B. subtilis, B. taeansis, B. tequilensis, B. thermantarcticus, B. thermoamylovorans, B. thermocloacae, B. thermolactis, B. thioparans, B. thuringiensis, B. tripoxylicola, B. tusciae, B. vallismortis, B. vedderi, B. vietnamensis, B. vireti, B. wakoensis, B. weihenstephanensis, B. xiaoxiensis*, and mixtures or blends thereof.

The PGPR and inoculants thereof disclosed herein may include *B. amyloliquefaciens* or a *Bacillus* species that is closely related to *B. amyloliquefaciens*. The partial sequence of *B. amyloliquefaciens* strain Chilli-1 16S ribosomal rDNA (GenBank Accession No. HQ021420.1) is provided herein as SEQ ID NO:1. A *Bacillus* species that is closely related to *B. amyloliquefaciens* may be defined as a species having a 16S rDNA sequence comprising SEQ ID NO:1 or comprising a 16S rDNA sequence having at least about 98% or 99% sequence identity to SEQ ID NO:1.

The PGPR and inoculants thereof disclosed herein may include *B. mojavensis* or a *Bacillus* species that is closely related to *B. mojavensis*. The partial sequence of *B. mojavensis* strain NBSL51 16S ribosomal rDNA (GenBank Accession No. JN624928.1) is provided herein as SEQ ID NO:2. A *Bacillus* species that is closely related to *B. mojavensis* may be defined as a species having a 16S rDNA sequence comprising SEQ ID NO:2 or comprising a 16S rDNA sequence having at least about 98% or 99% sequence identity to SEQ ID NO:2.

The PGPR and inoculants thereof disclosed herein may include *B. solisalsi* or a *Bacillus* species that is closely related to *B. solisalsi*. The partial sequence of *B. solisalsi* strain YC1 16S ribosomal rDNA (GenBank Accession No. NR_044387) is provided herein as SEQ ID NO:3. A *Bacillus* species that is closely related to *B. solisalsi* may be defined as a species having a 16S rDNA sequence comprising SEQ ID NO:3 or comprising a 16S rDNA sequence having at least about 91%, 92%, 93%, 94%, 95%, 96%, 97%, 98%, or 99% sequence identity to SEQ ID NO:3.

The PGPR and inoculants thereof disclosed herein may include *B. pumilus* or a *Bacillus* species that is closely related to *B. pumilus*. The partial sequence of *B. pumilus* strain TUB1 16S ribosomal rDNA (GenBank Accession No. HE613653.1) is provided herein as SEQ ID NO:4. A *Bacil-*

*lus* species that is closely related to *B. pumilus* may be defined as a species having a 16S rDNA sequence comprising SEQ ID NO:4 or comprising a 16S rDNA sequence having at least about 96%, 97%, 98%, or 99% sequence identity to SEQ ID NO:4.

The PGPR and inoculants thereof disclosed herein may include *B. simplex* or a *Bacillus* species that is closely related to *B. simplex*. The partial sequence of *B. simplex* strain NH.259 16S ribosomal rDNA (GenBank Accession No. EU627171.1) is provided herein as SEQ ID NO:5. A *Bacillus* species that is closely related to *B. simplex* may be defined as a species having a 16S rDNA sequence comprising SEQ ID NO:5 or comprising a 16S rDNA sequence having at least about 93%, 94%, 95%, 96%, 97%, 98%, or 99% sequence identity to SEQ ID NO:5.

The PGPR and inoculants thereof disclosed herein may include *B. subtilis* or a *Bacillus* species that is closely related to *B. subtilis*. The partial sequence of *B. subtilis* strain NH.259 16S ribosomal rDNA (GenBank Accession No. EU627171.1) is provided herein as SEQ ID NO:6. A *Bacillus* species that is closely related to *B. subtilis* may be defined as a species having a 16S rDNA sequence comprising SEQ ID NO:5 or comprising a 16S rDNA sequence having at least about 98%, or 99% sequence identity to SEQ ID NO:6.

In some embodiments of the inoculants disclosed herein comprising *Bacillus* bacteria, the *Bacillus* species is not *B. subtilis* and is not a *Bacillus* species that is closely related to *B. subtilis*. A *Bacillus* species that is not closely related to *B. subtilis* may be defined as a species having a 16S rDNA sequence that has no more than 99%, 98%, 97%, 96%, 95%, 94%, 93%, 92%, or 91% sequence identity to SEQ ID NO:5.

"Percentage sequence identity" may be determined by aligning two sequences of equivalent length using the Basic Local Alignment Search Tool (BLAST) available at the National Center for Biotechnology Information (NCBI) website (i.e., "bl2seq" as described in Tatiana A. Tatusova, Thomas L. Madden (1999), "Blast 2 sequences—a new tool for comparing protein and nucleotide sequences", FEMS Microbiol Lett. 174:247-250, incorporated herein by reference in its entirety). For example, percentage sequence identity between SEQ ID NO:1 and SEQ ID NO:5 may be determined by aligning these two sequences using the online BLAST software provided at the NCBI website.

"Percentage sequence identity" between two deoxyribonucleotide sequences may also be determined using the Kimura 2-parameter distance model which corrects for multiple hits, taking into account transitional and transversional substitution rates, while assuming that the four nucleotide frequencies are the same and that rates of substitution do not vary among sites (Nei and Kumar, 2000) as implemented in the MEGA 4 (Tamura K, Dudley J, Nei M & Kumar S (2007) MEGA4: Molecular Evolutionary Genetics Analysis (MEGA) software version 4.0. *Molecular Biology and Evolution* 24:1596-1599), preferably version 4.0.2 or later. The gap opening and extension penalties are set to 15 and 6.66 respectively. Terminal gaps are not penalized. The delay divergent sequences switch is set to 30. The transition weight score is 35 set to 0.5, as a balance between a complete mismatch and a matched pair score. The DNA weight matrix used is the IUB scoring matrix where x's and n's are matches to any IUB ambiguity symbol, and all matches score 1.9, and all mismatched score O.

As used herein, "Blend 8" refers to a mixture of *Bacillus* bacteria including *Bacillus amyloliquefaciens* strain AP-188, *Bacillus mojavensis* strain AP-209, *Bacillus solisalsi* strain AP-217, and *Bacillus amyloliquefaciens* strain AP-218. (See Table 1). As used herein, "Blend 9" refers to a mixture of *Bacillus* bacteria including *Bacillus amyloliquefaciens* strain AP-136, *Bacillus mojavensis* strain AP-188, *Bacillus solisalsi* strain AP-219, and *Bacillus amyloliquefaciens* strain AP-295.

The presently disclosed PGPR may be utilized to treat plants and induce VOC production in the treated plants. For example, the presently disclosed PGPR may be formulated as an inoculant for treating plants. The methods of treatment contemplated herein may include treating a plant directly including treating leaves, stems, or roots of the plant directly. The methods of treatment contemplated herein may include treating seeds of the plant, e.g., prior to the seeds being planted to produce a treated plant. The methods contemplated herein also may include treating a plant indirectly, for example, by treating soil or the environment surrounding the plant (e.g., in-furrow granular or liquid applications). Suitable methods of treatment may include applying an inoculant including the PGPR via high or low pressure spraying, drenching, and/or injection. Plant seeds may be treated by applying low or high pressure spraying, coating, immersion, and/or injection. After plant seeds have been thusly treated, the seeds may be planted and cultivated to produce plants. Plants propagated from such seeds may be further treated with one or more applications. Suitable application concentrations may be determined empirically. In some embodiments where the PGPR are applied as a spray to plants, suitable application concentrations may include spraying $10^6$-$10^{18}$ colony forming units (cfu) per hectare of plants, more commonly $10^7$-$10^{15}$ cfu per hectare. For coated seeds, in some embodiments, suitable application concentrations may be between $10^2$-$10^8$ cfu per seed, preferably $10^4$-$10^7$ cfu per seed. In other embodiments, the PGPR may be applied as a seedling root-dip or as a soil drench at a concentration of about $10^2$-$10^{12}$ cfu/ml, $10^4$-$10^{10}$ cfu/ml, or about $10^6$-$10^8$ cfu/ml.

The PGPR may be applied together with a suitable carrier in a composition (e.g., such as an inoculum). Suitable carriers may include, but are not limited to, water or other aqueous solutions, slurries, solids (e.g., peat, wheat, bran, vermiculite, and pasteurized soil) or dry powders. In some embodiments, the composition includes $10^2$-$10^{12}$ cfu per ml carrier, or $10^4$-$10^{10}$ cfu per ml carrier, or $10^6$-$10^8$ cfu per ml carrier. The composition may include additional additives including buffering agents, surfactants, adjuvants, or coating agents.

The presently disclosed methods may be performed in order to modify insect behavior towards a treated plant. As used herein, "modifying" insect behavior may include reducing or preventing negative insect behavior and/or increasing positive insect behavior. Reducing or preventing negative insect behavior may include reducing or preventing damage from insects. For example, the methods may be practiced to reduce or prevent feeding of herbivorous insects on a treated plant. Preferably, the methods reduce feeding on a treated plant versus an untreated plant by at least about 10%, 20%, 30%, 40%, 50%, 60%, 70%, 80%, or 90%. Reduction in feeding may be measured by comparing body mass of larvae feeding on treated plants versus untreated plants over a period of time. Reduction in feeding also may be measured by comparing mass of the plant lost due to insect feeding per time. The methods also may be practiced to reduce or prevent egg-laying of herbivorous insects on a treated plant. Preferably, the methods reduce egg-laying (i.e., oviposition) on a treated plant versus an untreated plant by at least about 10%, 20%, 30%, 40%, 50%, 60%, 70%, 80%, or 90%. Reduction in egg-laying may be measured by comparing egg-laying per insect (e.g., total number of eggs and/or total number of egg batches) on a treated plant versus an untreated plant. Herbivorous insects whose behavior may be modified by the presently disclosed methods may include, but are not limited to, *Spodoptera exigua* and *Pieris rapae*. The methods also may be practiced to attract natural enemies of insects to treated plants, including but not limited to predatory insects or insect parasitoids. Predatory insects may include, but are not limited to, lady beetles (i.e., Coccinelidae, assassin bugs (i.e., Reduviidae), big-Eyed bugs (i.e., Geocoridae), minute pirate bug (i.e., Antrocoridae), damsel bug (i.e., Nabidae), lacewings (i.e., Neuroptera), and predatory mites (i.e., Phytoseiidae). Insect parasitoids may include, but are not limited to, Brachonid wasps (e.g. *Cotesia marginiventris, Microplitis croceipes, Cotesia rubecula,* and *Aphidius colemani*), Ichneumonid wasps, Chalcid wasps (e.g., *Eretmocerus* spp., and *Encarsia formosa*), and Tachinid flies.

ILLUSTRATIVE EMBODIMENTS

The following embodiments are illustrative and are not intended to limit the claimed subject matter.

Embodiment 1. Isolated plant growth producing rhizobacteria (PGPR) that induce production of one or more volatile organic compounds (VOCs) by a plant that has been treated with the PGPR, and optionally the PGPR are selected from genus selected from a group consisting of *Actinobacter, Alcaligenes, Bacillus, Burkholderia, Buttiauxella, Enterobacter, Klebsiella, Kluyvera, Pseudomonas, Rahnella, Ralstonia, Rhizobium, Serratia, Stenotrophomonas, Paenibacillus,* and *Lysinibacillus.*

Embodiment 2. The PGPR according to embodiment 1 or 2, wherein the one or more VOCs comprise one or more compounds selected from a group consisting of The PGPR and inoculants thereof.

Embodiment 3. The PGPR according to any of the preceding embodiments, wherein the one or more VOCs modify behavior of an insect exposed to the one or more VOCs.

Embodiment 4. The PGPR according to any of the preceding embodiments, wherein the insect is an herbivore and the one or more VOCs reduce egg-laying of the insect on the plant.

Embodiment 5. The PGPR according to any of the preceding embodiments, wherein the insect is an herbivore and the one or more VOCs reduce feeding of the insect on the plant.

Embodiment 6. The PGPR according to any of the preceding embodiments, wherein the insect is a predator or a parasitoid and the one or more VOCs attract the predator or the parasitoid to the plant.

Embodiment 7. The PGPR according to any of the preceding embodiments, wherein the PGPR are *Bacillus* bacteria selected from a group consisting of *B. acidiceler, B. acidicola, B. acidiproducens, B. aeolius, B. aerius, B. aerophilus, B. agaradhaerens, B. aidingensis, B. akibai, B. alcalophilus, B. algicola, B. alkalinitrilicus, B. alkalisediminis, B. alkalitelluris, B. altitudinis, B. alveayuensis, B. amyloliquefaciens, B. anthracis, B. aquimaris, B. arsenicus, B. aryabhattai, B. asahii, B. atrophaeus, B. aurantiacus, B. azotoformans, B. badius, B. barbaricus, B. bataviensis, B. beijingensis, B. benzoevorans, B. beveridgei, B. bogoriensis, B. boroniphilus, B. butanolivorans, B. canaveralius, B. carboniphilus, B. cecembensis, B. cellulosilyticus, B. cereus, B. chagannorensis, B. chungangensis, B. cibi, B. circulans, B. clarkii, B. clausii, B. coagulans, B. coahuilensis, B. cohnii, B. decisifrondis, B. decolorationis, B. drentensis, B. farraginis, B. fastidiosus, B. firmus, B. flexus, B. foraminis, B. fordii, B. fortis, B. fumarioli, B. funiculus, B. galactosidilyticus, B. galliciensis, B. gelatini, B. gibsonii, B. ginsengi, B. ginsengihumi, B. graminis, B. halmapalus, B. halochares, B. halodurans, B. hemicellulosilyticus., B. herbertsteinensis, B. horikoshi, B. horneckiae, B. horti, B. humi, B. hwajinpoensis, B. idriensis, B. indicus, B. infantis, B. infernus, B. isabeliae, B. isronensis, B. jeotgali, B. koreensis, B. korlensis, B. kribbensis, B. krulwichiae, B. lehensis, B. lentus, B. licheniformis, B. litoralis, B. locisalis, B. luciferensis, B. luteolus, B. macauensis, B. macyae, B. mannanilyticus, B. marisflavi, B. marmarensis, B. massiliensis, B. megaterium, B. methanolicus, B. methylotrophicus, B. mojavensis, B. muralis, B. murimartini, B. mycoides, B. nanhaiensis, B. nanhaiisediminis, B. nealsonii, B. neizhouensis, B. niabensis, B. niacini, B. novalis, B. oceanisediminis, B. odysseyi, B. okhensis, B. okuhidensis, B. oleronius, B. oshimensis, B. panaciterrae, B. patagoniensis, B. persepolensis, B. plakortidis, B. pocheonensis, B. polygoni, B. pseudoalcaliphilus, B. pseudofirmus, B. pseudomycoides, B. psychrosaccharolyticus, B. pumilus, B. qingdaonensis, B. rigui, B. ruris, B. safensis, B. salarius, B. saliphilus, B. schlegelii, B. selenatarsenatis, B. selenitireducens, B. seohaeanensis, B. shackletonii, B. siamensis, B. simplex, B. siralis, B. smithii, B. soli, B. solisalsi, B. sonorensis, B. sporothermodurans, B. stratosphericus, B. subterraneus, B. subtilis, B. taeansi, B. tequilensis, B. thermantarcticus, B. thermoamylovorans, B. thermocloacae, B. thermolactis, B. thioparans, B. thuringiensis, B. tripoxylicola, B. tusciae, B. vallismortis, B. vedderi, B. vietnamensis, B. vireti, B. wakoensis, B. weihenstephanensis, B. xiaoxiensis,* and mixtures or blends thereof.

Embodiment 8. The *Bacillus* bacteria according to embodiment 7, wherein the bacteria have a 16S rDNA nucleic acid sequence comprising SEQ ID NO:1, SEQ ID NO:2, SEQ ID NO:3, SEQ ID NO:4, SEQ ID NO:5, or SEQ ID NO:6.

Embodiment 9. The *Bacillus* bacteria according to embodiment 7, wherein the bacteria have a 16S rDNA nucleic acid sequence that is at least 98% identical to SEQ ID NO:1.

Embodiment 10. The *Bacillus* bacteria according to any of embodiments 7-9, wherein the bacteria have a 16S rDNA nucleic acid sequence that is at least 98% identical to SEQ ID NO:2.

Embodiment 11. The *Bacillus* bacteria according to any of embodiments 7-10, wherein the bacteria have a 16S rDNA nucleic acid sequence that is at least 91% identical to SEQ ID NO:3.

Embodiment 12. The *Bacillus* bacteria according to any of embodiments 7-11, wherein the bacteria have a 16S rDNA nucleic acid sequence that is at least 96% identical to SEQ ID NO:4.

Embodiment 13. The *Bacillus* bacteria according to any of embodiments 7-12, wherein the bacteria have a 16S rDNA nucleic acid sequence that is at least 93% identical to SEQ ID NO:5.

Embodiment 14. The *Bacillus* bacteria according to any of embodiments 7-13, wherein the bacteria have a 16S rDNA nucleic acid sequence that is at least 98% identical to SEQ ID NO:6.

Embodiment 14. The *Bacillus* bacteria according to embodiment 7, wherein the bacteria are selected from a group consisting of *Bacillus amyloliquefaciens, Bacillus mojavensis, Bacillus solisalsi, Bacillus pumilus, Bacillus simplex, Bacillus subtilis* and mixtures thereof.

Embodiment 15. The *Bacillus* bacteria according to embodiment 7, wherein the bacteria are *Bacillus amyloliquefaciens*.

Embodiment 16. The *Bacillus* bacteria according to embodiment 15, wherein the bacteria are selected from a group consisting of *Bacillus amyloliquefaciens* strain AP-136, *Bacillus amyloliquefaciens* strain AP-188, *Bacillus amyloliquefaciens* strain AP-218, *Bacillus amyloliquefaciens* strain AP-219, and *Bacillus amyloliquefaciens* strain AP-295.

Embodiment 17. The *Bacillus* bacteria according to embodiment 7, wherein the bacteria are *Bacillus mojavensis*.

Embodiment 18. The *Bacillus* bacteria according to embodiment 17, wherein the bacteria are *Bacillus mojavensis* strain AP-209.

Embodiment 19. The *Bacillus* bacteria according to embodiment 7, wherein the bacteria are *Bacillus solisalsi*.

Embodiment 20. The *Bacillus* bacteria according to embodiment 19, wherein the bacteria are *Bacillus solisalsi* strain AP-217.

Embodiment 21. The *Bacillus* bacteria according to embodiment 7, wherein the bacteria are *Bacillus pumilus*.

Embodiment 22. The *Bacillus* bacteria according to embodiment 21, wherein the bacteria are *Bacillus pumilus* strain INR7.

Embodiment 23. The *Bacillus* bacteria according to embodiment 7, wherein the bacteria are *Bacillus simplex*.

Embodiment 24. The *Bacillus* bacteria according to embodiment 23, wherein the bacteria are *Bacillus simplex* strain ABU 288.

Embodiment 25. The *Bacillus* bacteria according to embodiment 7, wherein the bacteria are *Bacillus subtilis* strain MBI 600.

Embodiment 26. The *Bacillus* bacteria according to embodiment 7, wherein the bacteria comprise a mixture of *Bacillus* species.

Embodiment 27. An inoculant for a plant comprising the PGPR of any of the preceding embodiments and a carrier.

Embodiment 28. The inoculant of embodiment 27 further comprising a phytohormone, an anti-microbial compound, or both.

Embodiment 29. The inoculant of embodiment 28, wherein the phytohormone is selected from a group consisting of acetoin, 2,3-butanediol, and indole-acetic acid and the anti-microbial compound is selected from a group consisting of phenylethanol and 4-hydroxybenzoate.

Embodiment 30. A method of modifying insect behavior towards a plant, the method comprising a administering the inoculant of any of embodiments 27-29 to the plant, to seeds of the plant, or to soil surrounding the plant.

Embodiment 31. The method according to embodiment 30, wherein the insect is an herbivore and the method reduces egg-laying of the insect on the plant.

Embodiment 32. The method according to embodiment 30 or 31, wherein the insect is an herbivore and the method reduces feeding of the insect on the plant.

Embodiment 33. The method according to any of embodiments 30-32, wherein the insect is a predator or a parasitoid and the method attracts the predator or parasitoid to the plant.

Embodiment 34. The method according to any of embodiments 30-33, wherein the plant is selected from a group consisting of alfalfa, rice, barley, rye, cotton, sunflower, peanut, corn, potato, sweet potato, bean, pea, lentil chicory, lettuce, endive, cabbage, brussel sprout, beet, parsnip, turnip, cauliflower, broccoli, turnip, radish, spinach, onion, garlic, eggplant pepper, celery, carrot, squash, pumpkin, zucchini, cucumber, apple, pear, melon, citrus, strawberry, grape, raspberry, pineapple, soybean, canola, oil seed rape, spring wheat, winter wheat, tobacco, tomato, sorghum, and sugarcane.

EXAMPLES

The following Examples are illustrative and are not intended to limit the scope of the claimed subject matter.

Example 1

Effects of Plant Growth-Promoting Rhizobacteria on Induction of Cotton Plant Volatiles and Attraction of Parasitoids Abstract Parasitic wasps (parasitoids) are known to utilize as host location cues various types of host-related volatile signals. These volatile signals could be plant-based, originate from the herbivore host, or be produced from an interaction between herbivores and their plant host. The success of parasitoids in suppressing pest populations depends on their ability to locate hosts in a complex olfactory and visual environment. Despite the intense interest in host-parasitoid interactions, certain aspects of olfactory communication in this group of insects are not well understood.

Here, studies were conducted to evaluate the potential of plant growth-promoting rhizobacteria (PGPR) on the induction of cotton volatiles and consequences for response of parasitoids. Three PGPR treatments were evaluated: i) *Bacillus pumilis* strain INR-7 and two blends of *Bacillus* bacteria. An untreated (water) control was also tested. There were quantitative and qualitative differences in headspace volatiles collected from PGPR-treated and untreated cotton plants. A total of eleven peaks representing VOCs were detected from headspace of PGPR-treated cotton plants but only three peaks were detected in untreated cotton plants. Differences in root growth between PGPR-treated vs. untreated plants were recorded.

Introduction

Plant Growth-Promoting Rhizobacteria (PGPR) represent a wide range of root-colonizing bacteria whose application is often associated with increased rates of plant growth (Kloepper 1992, Zehnder et al. 1997, Kloepper et al. 2004), suppression of soil pathogens (Schippers et al. 1987, Burkett-Cadena et al. 2008), and the induction of systemic resistance against insect pests (van Loon et al. 1998, Kloepper et al. 1999, Ramamoorthy et al. 2001, Zehnder et al. 2001, Ryu et al. 2004, Ji et al. 2006). PGPR-based inoculants include formulations containing a single strain, a mixture of two strains, or complex mixtures of *Bacillus* spp. (Lucy et al. 2004, Kloepper and Ryu, 2006). The effects of application of PGPR on induction of volatile organic compounds (VOCs) in treated plants are virtually unexamined, despite evidence that induction of plant volatiles is dependent on many factors. The interactionsiotic factors which include plant hormones (de Bruxelles and Roberts, 2001, Thaler et al. 2002, Farmer et al. 2003, Ament et al. 2004), herbivore-derived elicitors (Mattiaci et al. 1995, Albom et al. 1997, Spiteller and Boland, 2003), and associated microorganisms including pathogens (Preston et al. 1999, Cardoza et al. 2002), as well as abiotic factors including wounding (Mithöfer et al. 2005), heavy metals (Mithöfer et al. 2004) and temperature and light (Takabayashi et al. 1994, Gouinguene and Turlings 2002). The lack of research related to the effects of PGPR on induction of plant volatiles is surprising given that PGPR are increasingly being applied to production of several field crops including cotton (*Gossypium hirsutum* L.), tomato (*Solanum lycopersicum* L.), watermelon (*Citrullus lanatus* Thunb.), and pearl millet (*Pennisetum glaucum*) in the USA or India (Glick 1995, Backman et al. 1997, Cleyet-Marcel et al. 2001, Kokalis-Burelle et al. 2003, Niranjan Raj et al. 2003, Burkett-Cadena et al. 2008). In 1997, Backman et al. reported that 60-75% of the US cotton crop was being treated with the PGPR product Kodiak®, a *Bacillus subtilis* product used for suppression of *Fusarium* and *Rhizoctonia* soil pathogens. PGPR have previously been used to treat agricultural crops on a large scale.

Like herbivores that use VOCs in their search for suitable host plants (Dicke et al. 2000), parasitic insects are also known to use blends of VOCs for foraging and host location of their herbivore hosts (Turlings et al. 1990, McCall et al. 1993, De Moraes et al. 1998). These VOCs can originate from the plant, herbivore host, or be the result of an interaction between herbivores and the plant (McCall et al., 1994, Cortesero et al. 1997). Plant-based VOCs are further categorized into green leaf volatiles (GLVs), which are released immediately in response to mechanical damage or at the beginning of herbivore feeding, and herbivore-induced plant volatiles (HIPVs), which are emitted as a delayed response to herbivore feeding damage. These blends of VOCs, which are highly attractive to parasitoids of cotton herbivores including *Microplitis croceipes* (Cresson) and *Cotesia marginiventris* (Cresson) (Hymenoptera: Braconidae), are released in response to caterpillar feeding (De Moraes et al. 1998, Chen and Fadamiro 2007, Ngumbi et al. 2009, 2010). It is possible that PGPR could affect VOC production in cotton with important consequences for foraging parasitoids and other chemically mediated insect-plant and tri-trophic interactions.

Here, the hypothesis that PGPR could elicit changes in cotton plant VOCs and alter the growth of cotton roots was tested. Additionally, it was hypothesized that parasitoids of cotton herbivores would show greater attraction to PGPR-treated cotton plants compared to untreated cotton plants via changes in the emission of VOCs. PGPR-treated and untreated cotton plants were grown under greenhouse conditions and headspace volatiles collected 4-6 weeks post planting. Coupled gas chromatography-mass spectrometry (GC-MS) was used to identify and analyze headspace volatiles from PGPR-treated and untreated cotton plants. A four-choice olfactometer was used to study the behavior of *M. croceipes* when presented with PGPR-treated plants versus untreated plants. To the inventors' knowledge, this is the first report of PGPR affecting the production of VOCs by cotton plants.

Materials and Methods

PGPR Strains. As shown in Table 1 a total of eight strains of *Bacillus* spp. (all from Auburn University) were used to develop the three PGPR treatments studied: i) *Bacillus pumilus* strain INR-7 (AP 18), ii) Blend 8, containing four strains of *Bacillus* spp. (AP 188, 209, 217 218), and iii) Blend 9, containing four strains of *Bacillus* spp. (AP 136, 188, 219, 295).

TABLE 1

PGPR Preparations

| PGPR Preparation | Identification |
| --- | --- |
| Blend 8 | *Bacillus amyloliquefaciens* strain AP-188 |
|  | *Bacillus mojavensis* strain AP-209 |
|  | *Bacillus solisalsi* strain AP-217 |
|  | *Bacillus amyloliquefaciens* strain AP-218 |
| Blend 9 | *Bacillus amyloliquefaciens* strain AP-136 |
|  | *Bacillus amyloliquefaciens* strain AP-188 |
|  | *Bacillus amyloliquefaciens* strain AP-219 |
|  | *Bacillus amyloliquefaciens* strain AP-295 |
| INR-7 | *Bacillus pumilus* strain AP-18 |

Plants. Conventional variety (*G. hirsutum*) Max-9 cotton seeds (All-Tex Seed, Inc.) were grown individually in round plastic pots (9 cm high, 11 cm diameter) filled with a top soil/vermiculite/peat moss mixture. The seeds were then grown in individual pots (9 cm high, 11 cm diameter) in a greenhouse (Auburn University Plant Science Greenhouse Facility) at 25° C.±10, 15:9 h (L/D) photoperiod, and 50±10% relative humidity. PGPR treatments were applied at seeding (1 ml/seed) as aqueous spore suspensions ($1 \times 10^7$ spores/ml). Weekly, PGPR-treated plants received 1 ml additional treatments as an aqueous bacterial suspension ($1 \times 10^9$ cfu/ml). Plants used for headspace volatile collections were 4 to 6 weeks old from day of planting.

Insects. Parent cultures of *M. croceipes* were provided by the USDA-ARS, Insect Biology and Population Management Research Laboratory (Tifton, Ga.). *Microplitis croceipes* were reared on caterpillars of *Heliothis virescens* (Fab.) Lepidoptera: Noctuidae, its preferred host (Stadelbacher et al. 1984, King et al. 1985), using a procedure similar to that of Lewis and Burton (1970). Eggs purchased from Benzone Research (Carlisle, Pa., USA) were used to start a laboratory colony of *H. virescens* reared on a laboratory-prepared pinto bean diet (Shorey and Hale 1965). All colonies were maintained at 25±1° C., 75±5% RH, and under a L14:D10 photoperiod. Newly emerged *M. croceipes* adults were collected prior to mating, sexed, and placed in pairs of individuals of opposite sex (mated individuals) in a 6-cm diameter plastic Petri dish supplied with water and sugar sources. Water was provided by filling a 0.5 ml microcentrifuge tube with distilled water and threading a cotton string through a hole in the cap of the tube. About 5 drops (2 µl per drop) of 10% sugar solution were smeared on the inside of the Petri dish cover with a cotton-tipped applicator. Naïve parasitoids (aged 3-5 days) were used for the bioassays.

Collection and GC Analysis of Headspace Volatiles. The methodology and protocols used for volatile collection were similar to those reported by Gouinguené et al. (2005), but with some modifications. Headspace volatiles were collected both from PGPR-treated and untreated cotton plants as well as PGPR-treated and untreated caterpillar damaged cotton plants. In order to detect herbivore induced plant volatiles (HIPVs) from PGPR-treated and untreated plants, 30 $2^{nd}$ instar caterpillars of *Heliothis virescens* Fab. (Lepidoptera: Noctuidae) were allowed to feed on a potted cotton plant for 12 h prior to volatile collection. The pot with the potting soil was wrapped with aluminum foil to minimize evaporation of water and volatiles from the soil. The plant was then placed in a volatile collection chamber (Analytical Research Systems, Inc., Gainesville, Fla.) consisting of a 5 L glass jar. A purified (using activated charcoal) air stream of 500 ml/min was passed through the jar at room temperature for 24 hr. Headspace volatiles were collected using a trap containing 50 mg of Super-Q (Alltech Associates, Deerfield, Ill.) and eluted with 200 µl of methylene chloride. The elutions (200 µl) were stored in a freezer (at −20° C.) until use. Another container with potting soil but no plant was used to check for miscellaneous impurities and background noise. One µl of each headspace volatile extract was injected into a Shimadzu GC-17A equipped with a flame ionization detector (FID). The dimension of the capillary column used was as follows: Rtx-1MS, 0.25 mm I.D., 0.25 µm film thickness (Restek, Bellefonte, Pa.). Helium was used as carrier gas at a flow rate of 1 ml/min. The GC oven was programmed as follows: inject at 40° C., hold at 40° C. for 2 minutes, and then increase by 5° C./min to 200° C. for a total of 40 minutes. The temperatures of both the injector and detector were set at 200° C. Five replicates were carried out.

GC-MS Analysis. GC profiles of each plant treatment were later identified by GC-MS using an Agilent 7890A GC coupled to a 5975C Mass Selective Detector, with a HP-5 ms capillary column (30 m×0.25 mm I.D., 0.25 µm film thickness). One µl of each headspace extract was injected into the GC in splitless mode, using the GC conditions described above. Mass spectra were obtained using electron impact (EI, 70 eV). Identification of peaks was done using NIST 98 library (National Institute of Standards and Technology, Gaithersburg, Md.) and comparison with published GC profiles of cotton head space volatiles (Thompson et al. 1971, Loughrin et al. 1994, McCall et al. 1994). The structures of the identified compounds were confirmed using commercially available synthetic standards with purity>97% (as indicated on the labels) obtained from Sigma® Chemical Co. (St. Louis, Mo.).

Analysis of Cotton Root Growth. A separate experiment was carried out to determine if treatment of cotton with PGPR would lead to differences in cotton root growth. One ml of PGPR (INR-7, Blend 8, and Blend 9) at spore concentrations of $10^7$ was applied to cotton seed. The PGPR-treated seeds were then grown in individual pots (15 cm high, 21 cm diameter) in a greenhouse (Auburn University Plant Science Greenhouse Facility) at 25° C.±10, 15:9 h (L/D) photoperiod, and 50±10% relative humidity. Seeds were planted in a top soil/vermiculite/peat moss mixture. Additionally, every week, 1 ml of aqueous bacterial suspension ($10^9$) colony forming units (cfu/ml) was applied. Plants used for cotton root growth analysis were two weeks old. After washing roots, an analysis of root architecture was made on each plant's rooting system using the system of Regent Instruments, Inc. (Sainte-Foy, Quebec), which consists of scanner model LA 1600+ and WinRhizo software (version 2004a). Data from the resulting analyses were collected for two root parameters: root surface area and root volume (0-0.5 and 0.5-1.0 mm). Data on root dry weight were also collected. Eight replicates were done.

Four-Choice Olfactometer Bioassays with Parasitoids. Attraction of *M. croceipes* to odors of PGPR-treated vs. untreated plants, as well as PGPR-treated caterpillar-damaged vs. undamaged plants, was assessed in four-choice olfactometer bioassays (Analytical Research Systems, Gainesville, Fla.). The apparatus was similar to the system described by Pettersson (1970) and Kalule and Wright (2004). It consists of a central chamber with orifices at the four corners through which purified and humidified air was drawn in, creating four potential odor fields, and a central orifice where mixing of the airflow from the arms occurred. A constant airflow of 500 ml/min was maintained through each of the four orifices at the corners of the olfactometer. Mixtures of air from the control arms and volatile odors from the treatment arms were drawn out from the olfactometer, through the central orifice, with a constant airflow of 2.5 l/min. Volatile odors emanated from plants that were 4-6 weeks old post-planting. The pot with the potting soil was wrapped with aluminum foil to minimize evaporation of water and volatiles. The plants were then placed in 5 L glass jar (32 cm high, 14.5 cm diameter) volatile collection chambers (Analytical Research Systems, Inc., Gainesville, Fla. USA) and purified air (500 ml/min) was passed through the chambers and into each of the 4 orifices at the corners of the olfactometer.

Naïve three-to-five-day-old female *M. croceipes* were used in all experiments. A wasp was removed from the cage with an aspirator and introduced singly into a glass tube (1.5 cm). The glass tube was connected to the central orifice of the olfactometer to expose the wasp to the volatile odors/air mixtures. Once in the chamber, a parasitoid was given 15 min to make a choice among the four air fields. If the parasitoid had not made a choice within this duration, it was removed, discarded, and not included in the analyses. In order to remove any directional bias in the chamber, the olfactometer and the position of plants were rotated after eight parasitoids had been tested. A total of 32 parasitoids were tested each day (8 parasitoids per rotation). Three sets of four-choice olfactometer experiments were conducted to test whether females *M. croceipes* responded differently to uninfested versus infested cotton plants and PGPR-treated versus untreated cotton plants. In the first experiment the following two treatments and two controls were compared: (1) PGPR INR7-treated plant (2) PGPR Blend 9 treated plant (3) Untreated (control) plant, (4) blank control (empty chamber). Based on the results of the first experiment, which showed significant attraction of the parasitoid to PGPR Blend 9-treated plants as compared to untreated (control)

plants (FIG. 6), a second experiment was conducted to determine if PGPR treatment is as effective as caterpillar infestation/damage in attracting parasitoids to plants. For this experiment, the PGPR treatment (Blend 9) was selected based on results from the previous experiment, and volatile odors from the following were compared: (1) PGPR Blend 9-treated plant infested, (2) PGPR Blend 9-treated plant uninfested, (3) Untreated (control) plant infested, and (4) control (empty chamber). Each plant was infested with 30 *H. virescens* caterpillars. A third experiment was conducted based on the result of the second experiment, which showed that untreated (control) plants infested with 30 caterpillars were as attractive to parasitoids as PGPR Blend 9-treated plants infested with 30 caterpillars. This suggests that PGPR treatment may be signaling a lower level of caterpillar damage than the level tested in the second experiment. To test this hypothesis and determine if PGPR treatment is as good as low level of caterpillar damage in attracting parasitoids to plants, the same treatments and controls tested in experiment 2 were compared but each infested plant was infested with two *H. virescens* caterpillars.

Four-choice olfactometer bioassays were carried out between 10:00 and 18:00 hrs each day at 25±1° C., 60±5% r.h. and 250 lux. The first experiment was replicated five times, while experiments 2 and 3 were replicated four times. For each replicate, a new set of plants was used.

Statistical Analysis. Data met the key assumptions of Analysis of Variance and thus were not transformed prior to analysis. Significant differences in the amounts of each volatile component emitted by PGPR-treated (*Bacillus pumilis* strain INR-7, Blend 8, and Blend 9) treated and untreated plants were established using Analysis of Variance (ANOVA) followed by the Tukey-Kramer HSD multiple comparison test (P<0.05, JMP 7.0.1, SAS Institute 2007). Significant differences in cotton root growth were established by ANOVA followed by the Tukey-Kramer HSD multiple comparison test (P<0.05, JMP 7.0.1, SAS Institute 2007). Four-choice olfactometer data were analyzed by one-way ANOVA followed by the Tukey-Kramer HSD multiple comparison test (P<0.05, JMP 7.0.1, SAS Institute 2007).

Results

GC and GC-MS Analyses of Headspace Volatiles. The GC profiles of the extracts of headspace volatiles from PGPR-treated and untreated cotton plants are shown in FIG. 1. A total of 11 peaks (volatile components) were detected in the headspace of PGPR-treated (INR-7, Blend 8, and Blend 9) cotton plants (FIG. 1). These peaks, as identified by GC-MS, included α-pinene, β-pinene, β-myrcene, cis-3-hexenyl acetate, limonene, (β)-ocimene, linalool, caryophyllene, α-humulene, and β-farnesene. Most of these peaks were not detected or were detected in insignificant amounts in the headspace of untreated cotton plants (FIG. 1). Only three peaks (components) were detectable in untreated cotton plants and were identified by GC-MS as α-pinene, cis-3-hexenyl acetate, and caryophyllene. However, all three components were detected in much greater amounts in the headspace of PGPR-treated plants. Additionally, significant differences were recorded between the PGPR treatments. (See Table 2).

TABLE 2

Composition of headspace volatiles emitted by untreated (control) cotton plants vs. cotton plants treated with strain INR-7, Blend 8, or Blend 9

| ID | Compound[a] | Untreated (control) cotton plants | Cotton plants treated with PGPR strain INR-7 | Cotton plants treated with PGPR Blend 8 | Cotton plants treated with PGPR Blend 9 |
|---|---|---|---|---|---|
| 1 | α-pinene | 58 ± 12$^d$ | 12,960 ± 2288$^a$ | 9,766 ± 1011$^b$ | 5,714 ± 519$^c$ |
| 2 | β-pinene | 0$^d$ | 2,739 ± 1782$^a$ | 2,298 ± 280$^b$ | 786 ± 132$^c$ |
| 3 | β-myrcene | 0$^d$ | 4,084 ± 105$^a$ | 3,044 ± 94$^b$ | 864 ± 148$^c$ |
| 4 | cis-3-hexenyl acetate | 62 ± 5$^d$ | 3,730 ± 79$^a$ | 1,884 ± 107$^b$ | 700 ± 143$^c$ |
| 5 | limonene | 0$^b$ | 2,266 ± 146$^a$ | 2,230 ± 122$^a$ | 2,188 ± 137$^a$ |
| 6 | β-ocimene | 0$^c$ | 4,000 ± 79$^a$ | 3,036 ± 116$^b$ | 0$^c$ |
| 7 | linalool | 0$^c$ | 456 ± 59$^b$ | 2,050 ± 73$^a$ | 1,964 ± 94$^a$ |
| 8 | unknown | 0$^c$ | 2,962 ± 123$^a$ | 2,352 ± 210$^b$ | 2,962 ± 45$^a$ |
| 9 | caryophyllene | 75 ± 10$^d$ | 6,928 ± 787$^b$ | 8,380 ± 842$^a$ | 3,182 ± 200$^c$ |
| 10 | α-humulene | 0$^c$ | 1,844 ± 136$^a$ | 1,811 ± 120$^a$ | 288 ± 42$^b$ |
| 11 | β-farnesene | 0$^c$ | 1,836 ± 96$^a$ | 1,830 ± 52$^a$ | 284 ± 56$^b$ |

Note:
Volatiles were collected for 24 h.
[a]In order of elution during gas chromatography
[b]Values (amount emitted) are mean ng amount ± SE of five replicates
Means across the same row followed by different letters are significantly different (P < 0.05, ANOVA)

Figure 2:
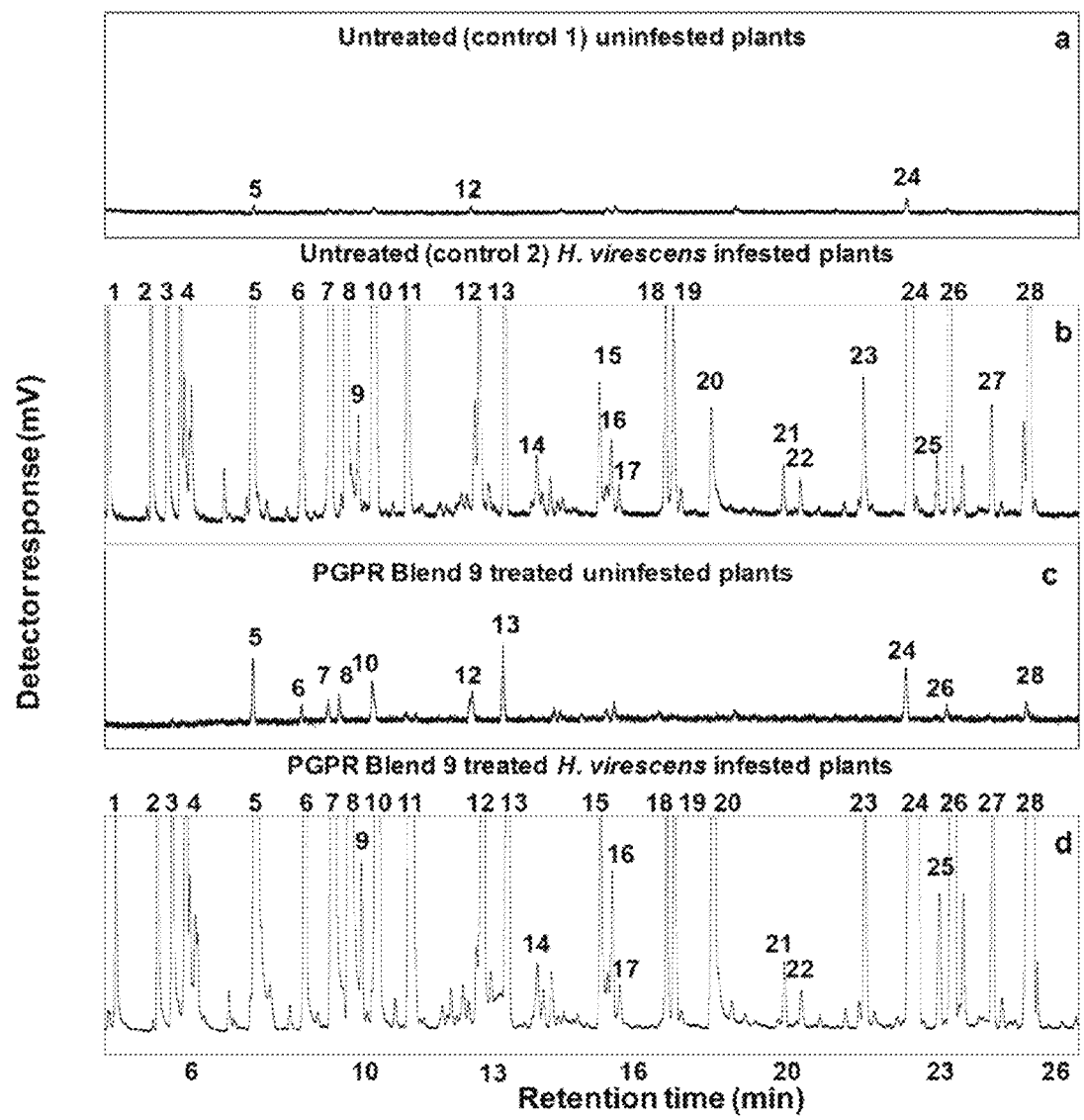

PGPR strain INR-7 treated cotton plants released significantly more α-pinene, β-pinene, β-myrcene, cis-3-hexenyl acetate, and β-ocimene than Blend 8 or Blend 9 treated plants (Table 2, FIG. 1). Additionally, β-ocimene was not detected in Blend 9 (Table 2, FIG. 1). FIG. 2 shows the GC profiles of the headspace volatiles emitted by the following four treatments: untreated (control) uninfested plants, untreated (control) *H. virescens* infested plants, PGPR Blend 9 treated uninfested plants, and PGPR Blend 9 treated *H. virescens* infested plants.

Identical peaks (28) were detected in extracts of untreated (control) *H. virescens* infested plants and PGPR Blend 9 treated *H. virescens* infested plants (Table 3, FIG. 2). However, 10 peaks (components) were detected in PGPR Blend 9 treated uninfested plants compared with only 3 peaks detected in untreated (control) uninfested plants (FIG. 2).

TABLE 3

Composition of headspace volatiles emitted by untreated (control) uninfested cotton plants vs. untreated (control) *H. virescens* infested plants, PGPR Blend 9 treated uninfested plants, or PGPR Blend 9 treated *H. virescens* infested plants

| ID | Compound | Untreated (control) uninfested cotton plants | Untreated (control) *H. virescens* infested plants | PGPR Blend 9 treated uninfested plants | PGPR Blend 9 treated *H. virescens* infested plants |
|---|---|---|---|---|---|
| 1 | cis-3-hexenal | 0 | 39,740 ± 2985[a] | 0 | 38,844 ± 3397[a] |
| 2 | trans-2-hexenal | 0 | 63,131 ± 2653[a] | 0 | 63,020 ± 2527[a] |
| 3 | cis-3-hexen-1-ol | 0 | 15,720 ± 916[a] | 0 | 15,340 ± 1262[a] |
| 4 | trans-2-hexen-1-ol | 0 | 68,602 ± 2774[a] | 0 | 68,802 ± 2451[a] |
| 5 | α-pinene | 58 ± 12[c] | 93,110 ± 1345[a] | 5,714 ± 519[b] | 95,110 ± 1081[a] |
| 6 | β-pinene | 0 | 58,039 ± 4522[a] | 786 ± 132[b] | 57,839 ± 1606[a] |
| 7 | myrcene | 0 | 120,239 ± 6930[a] | 864 ± 148[b] | 119,979 ± 6500[a] |
| 8 | cis-3-hexenyl acetate | 0 | 161,450 ± 5000[a] | 700 ± 143[b] | 163,510 ± 4300[a] |
| 9 | trans-2-hexenyl acetate | 0 | 98,814 ± 1892[a] | 0 | 99,270 ± 1504[a] |
| 10 | limonene | 0 | 110,272 ± 3614[a] | 2,188 ± 137[b] | 110,059 ± 3460[a] |
| 11 | β-ocimene | 0 | 120,177 ± 3147[a] | 0 | 120,466 ± 4200[a] |
| 12 | linalool | 62 ± 16[c] | 18,343 ± 1704[a] | 1,964 ± 94[b] | 18,863 ± 1660[a] |
| 13 | unknown | 0 | 57,320 ± 2531[a] | 2,962 ± 45[b] | 60,720 ± 2100[a] |
| 14 | 4,8-dimethyl-1,3,7-nonatriene | 0 | 20,920 ± 2166[a] | 0 | 20,736 ± 2109[a] |
| 15 | cis-3-hexenyl butyrate | 0 | 106,285 ± 2136[a] | 0 | 108,725 ± 4628[a] |
| 16 | trans-2-hexenyl butyrate | 0 | 88,170 ± 2420[a] | 0 | 90,730 ± 3256[a] |
| 17 | n-decanal | 0 | 4,700 ± 541[a] | 0 | 4,900 ± 877[a] |
| 18 | cis-3-hexenyl-2-methyl butyrate | 0 | 135,100 ± 6607[a] | 0 | 135,695 ± 6779[a] |
| 19 | trans-2-hexenyl-2-methyl butyrate | 0 | 128,350 ± 5055[a] | 0 | 126,950 ± 6136[a] |
| 20 | indole | 0 | 58,430 ± 2051[a] | 0 | 68,430 ± 1934[a] |
| 21 | isobutyl tiglate | 0 | 15,700 ± 1139[a] | 0 | 15,500 ± 1028[a] |
| 22 | 2-hexenyl tiglate | 0 | 6,700 ± 190[a] | 0 | 6,620 ± 97[a] |
| 23 | cis-jasmone | 0 | 55,811 ± 928[a] | 0 | 69,200 ± 1484[a] |
| 24 | caryophyllene | 75 ± 10 | 172,500 ± 6461[a] | 3,182 ± 200[c] | 186,500 ± 6825[b] |
| 25 | α-trans bergamotene | 0 | 15,778 ± 832[b] | 0 | 17,578 ± 817[a] |
| 26 | α-farnesene | 0 | 38,145 ± 1754[a] | 288 ± 42[b] | 39,345 ± 1500[a] |
| 27 | α-humulene | 0 | 32,400 ± 1023[a] | 0 | 34,800 ± 994[a] |
| 28 | β-farnesene | 0 | 47,979 ± 870[a] | 0 | 52,439 ± 1072[a] |

Note:
Volatiles were collected for 24 h.
[1]In order of elution during gas chromatography
[2]Values (amount emitted) are mean ng amount ± SE of five replicate extractions
Means across the same row followed by different letters are significantly different (P < 0.05, ANOVA).

Figure 3:
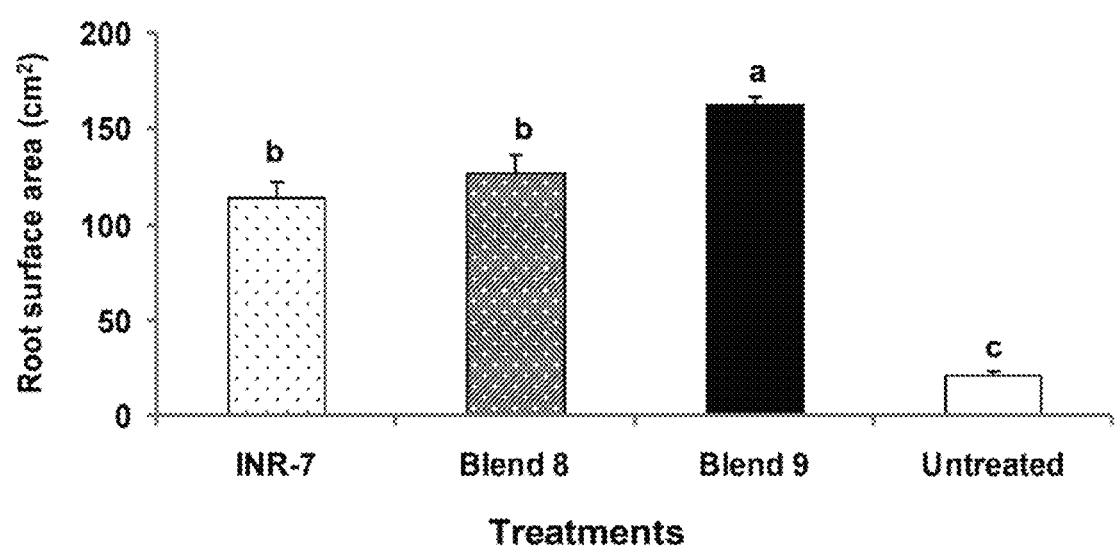
FIG. 3. Root surface area (cm$^2$) of untreated (control) cotton plants vs. cotton plants treated with PGPR strain INR-7, PGPR Blend 8, or PGPR Blend 9. Means followed by different letters are significantly different (P<0.05, ANOVA, Tukey-Kramer HSD multiple comparison test, n=8)
Figure 4:
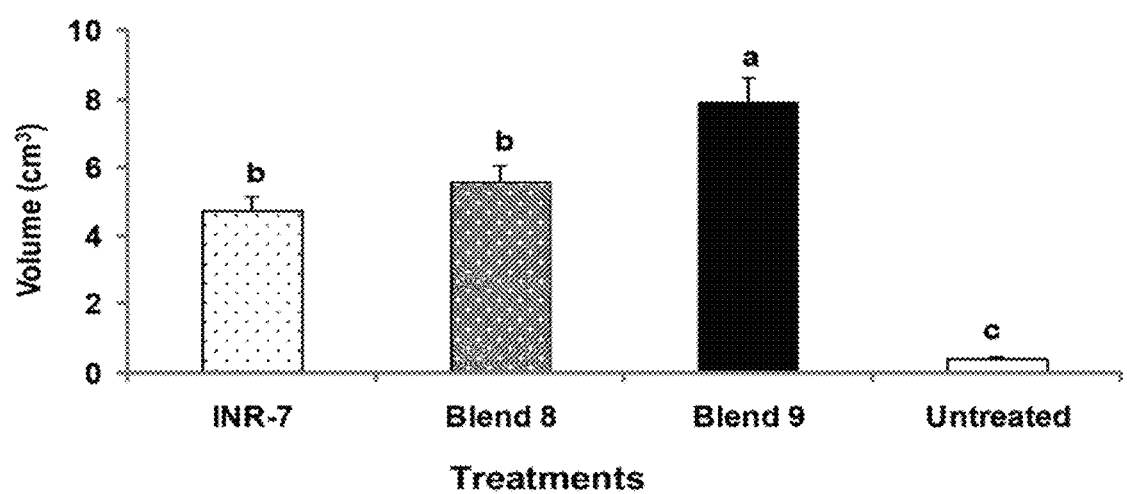
FIG. 4. Root volume (cm$^3$) of untreated (control) cotton plants vs. cotton plants treated with PGPR strain INR-7, PGPR Blend 8, or PGPR Blend 9. Means followed by different letters are significantly different (P<0.05, ANOVA, Tukey-Kramer HSD multiple comparison test, n=8).
Figure 5:
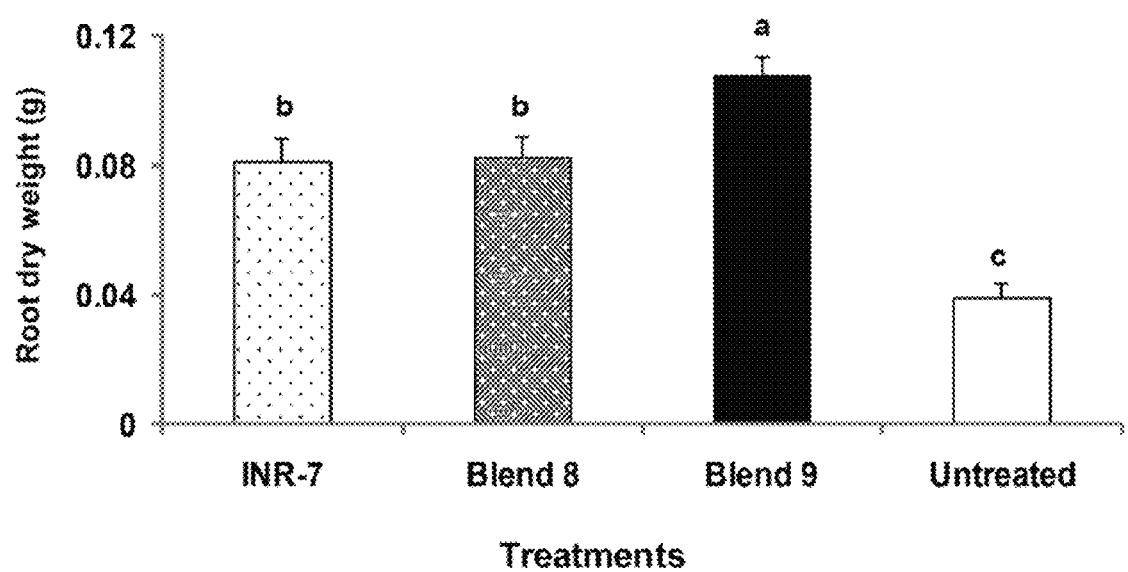
FIG. 5. Root dry weight (g) of untreated (control) cotton plants vs. cotton plants treated with PGPR strain INR-7, PGPR Blend 8, or PGPR Blend 9. Means followed by different letters are significantly different (P<0.05, ANOVA, Tukey-Kramer HSD multiple comparison test, n=8)

Analysis of Cotton Root Growth. Cotton root growth promotion resulting after PGPR treatment is shown in FIGS. 2, 3, and 4. Inoculation of cotton seeds with PGPR strains INR-7, Blend 8, and Blend 9, significantly promoted growth as compared to the untreated control. Significant differences were recorded among the treatments in root surface area ($F_{3,7}=74.78$, P<0.0001; FIG. 3), root volume ($F_{3,7}=50.42$, P<0.0001; FIG. 4), and root dry weight ($F_{3,7}=28.07$, P<0.0001; FIG. 5). In all cases, Blend 9-treated plants had the highest root surface area, root volume, and root dry weight. INR-7 and Blend 8-treated plants also had significantly higher root growth parameters than untreated plants (FIGS. 3, 4 and 5).

Figure 6:
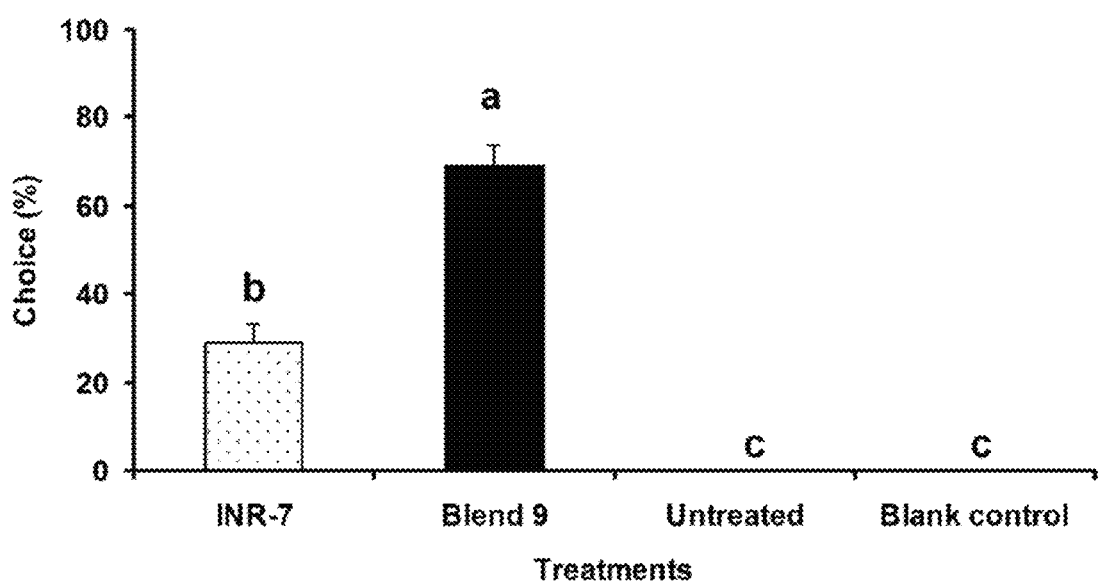
FIG. 6. Response of naïve female M. croceipes in a four-choice olfactometer to untreated (control) cotton plants vs. cotton plants treated with PGPR strain INR-7, PGPR Blend 9, or blank control (empty chamber). Thirty-two parasitoids were tested each day and replicated five times. Means followed by different letters are significantly different (P<0.05, ANOVA, Tukey-Kramer HSD multiple comparison test, n=5)
Figure 7:
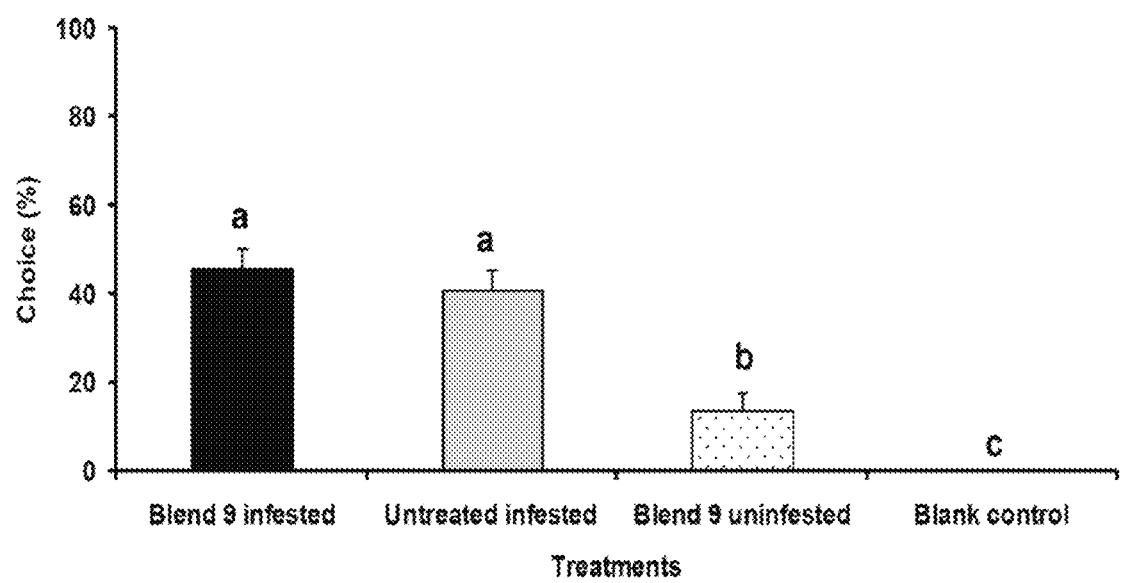
FIG. 7. Responses of naïve female M. croceipes in a four-choice olfactometer to untreated (control) cotton plants infested vs. cotton plants treated with PGPR Blend 9 infested, PGPR Blend 9 uninfested, or blank control (empty chamber). Plants were infested with 30 H. virescens caterpillars. Thirty-two parasitoids were tested each day and replicated four times. Means followed by different letters are significantly different (P<0.05, ANOVA, Tukey-Kramer HSD multiple comparison test, n=4)
Figure 8:
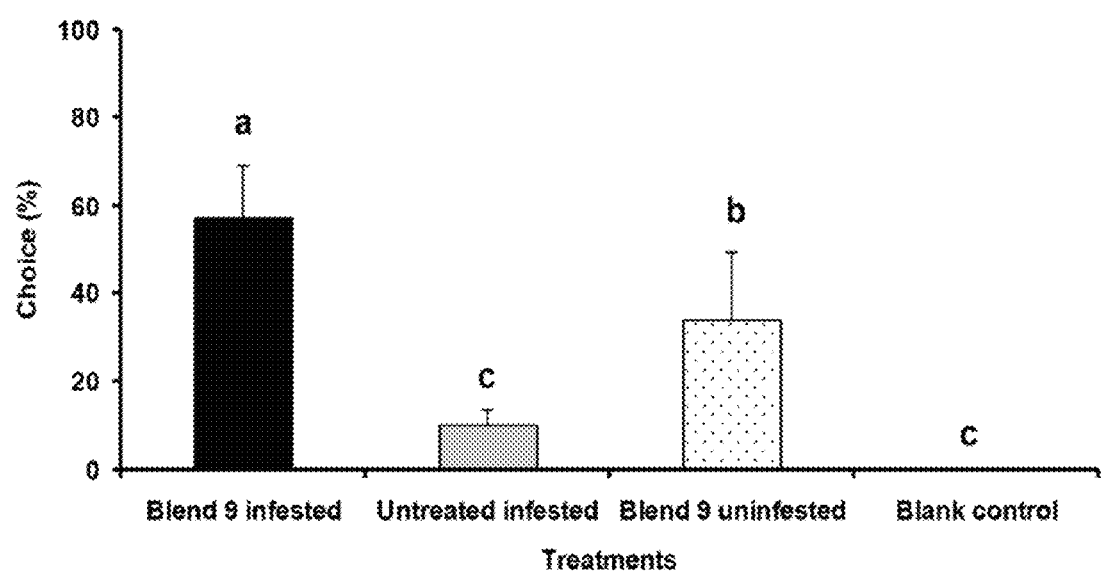
FIG. 8. Responses of naïve female M. croceipes in a four-choice olfactometer to untreated (control) cotton plants infested vs. cotton plants treated with PGPR Blend 9 infested, PGPR Blend 9 uninfested, or blank control (empty chamber). Plants were infested with two H. virescens caterpillars. Thirty-two parasitoids were tested each day and replicated four times. Means followed by different letters are significantly different (P<0.05, ANOVA, Tukey-Kramer HSD multiple comparison test, n=4)

Four-Choice Olfactometer Bioassays with Parasitoids. In the first experiment, significant differences were recorded in the response of female *M. croceipes* to the two treatments and two controls. Parasitoids were significantly ($F_{3,7}=106.64$, P<0.0001) more attracted to Blend 9-treated plants (69%) compared with INR-7 treated plants (29%), untreated (control) plants (0%), or blank control (empty chamber) (0%) (FIG. 6). Significant differences were also recorded among the treatments ($F_{3,12}=35.92$, P<0.0001) in experiment 2, which was designed to determine if PGPR treatment is as effective as caterpillar infestation/damage (30 *H. virescens* caterpillars) in attracting parasitoids to plants. As expected, PGPR Blend 9-treated plants infested with 30 caterpillars (46%) and untreated (control) plants infested with 30 caterpillars (41%) were highly attractive to parasitoids. However, parasitoids were more attracted to untreated (control) plants infested with 30 caterpillars (41%) than to uninfested PGPR Blend 9-treated plants (13%) (FIG. 7), suggesting that PGPR treatment was not as potent as infestation with 30 caterpillars in attracting parasitoids. The results of the third experiment, in which a lower level of infestation (2 *H. virescens* caterpillars per plant) was tested, also showed significant differences among the treatments and controls ($F_{3,12}=7.12$, P=0.0053). The most attractive treatment was PGPR Blend 9-treated plants infested with two caterpillars (58%). However, significantly more parasitoids were attracted to uninfested PGPR Blend 9 treated plant (25%) compared with untreated (control) plants infested with two caterpillars (15%) (FIG. 8). These results showed that PGPR treatment was at least as effective as low levels of caterpillar damage in attracting parasitoids to plants.

Discussion

These results show that plant growth-promoting rhizobacteria (PGPR) alter volatile organic compounds (VOCs) production in cotton plants. The discovery that PGPR alters the production of VOCs in cotton constitutes an unreported mechanism for the elicitation of plant volatile production by rhizobacteria. All tested PGPR treatments (INR7, Blend 8 and Blend 9) elicited the emission of VOCs that were not detected in untreated cotton plants. Eleven components were detected in the headspace of PGPR-treated plants. In the headspace of untreated plants, most of these compounds were not detected or were detected in insignificant amounts (only three were detected). In addition to altering VOC production, PGPR treatments also led to cotton plant root growth promotion, with Blend 9 showing the highest root growth promotion. PGPR have previously been reported to promote plant growth (including roots) in several plant species. Most intriguingly, results from the four-choice olfactometer experiments show that parasitoids were able to distinguish between PGPR treated and untreated plants, preferring the former over the latter.

The major components detected in headspace collections of PGPR-treated plants were: α-pinene, β-pinene, β-myrcene, cis-3-hexenyl acetate, limonene, β-ocimene, linalool, caryophyllene, α-humulene, and β-farnesene (Table 2, FIG. 1). These compounds have been reported before to be constituents of blends of VOCs emitted from caterpillar damaged cotton plants (Loughrin et al. 1994, De Moraes et al. 1998, Ngumbi et al. 2009). However, unlike previous reports, the PGPR-induced blend of VOCs is qualitatively different from VOCs emitted by caterpillar damaged plants (Table 3, FIG. 2). Differences in the quality of the blend of VOCs are defined as differences in the presence of specific compounds in the blend and/or ratio of the components. These results suggest that some VOCs, such as α-pinene, β-pinene, cis-3-hexenyl acetate, limonene, β-ocimene, linalool, caryophyllene, α-humulene, and β-farnesene may be elicited by PGPR. Previous studies have reported that VOC production in plants may be elicited by plant hormones (de Bruxelles and Roberts, 2001, Thaler et al. 2002, Farmer et al. 2003, Ament et al. 2004), herbivore-derived elicitors (Mattiaci et al. 1995, Alborn et al. 1997, Spiteller and Boland, 2003), pathogens (Cardoza et al. 2002), wounding (Mithöfer et al. 2005), and heavy metals (Mithöfer et al. 2004). These findings demonstrate that PGPR elicit the induction of VOCs and further studies are warranted to understand the mechanisms by which treatment of cotton plants with PGPR led to the release of VOCs that differ from untreated plants.

These data on cotton root analysis suggest that PGPR treatment enhanced cotton root growth. Increase in root weight growth as a result of PGPR treatment has been recorded for other crops, including sweet basil (*Ocimum basilicum* L.) and tomato (*Solanum lycopersicum* L.) (Kloepper 1992, Zehnder et al. 1997, Kloepper et al. 2004, Burkett-Cadena et al. 2008, Banchio et al. 2009, Humberto et al. 2010). PGPR have been applied to different crops for the purposes of growth enhancement and other positive effects in plants, such as seed emergence, tolerance to drought, and increase in weight of plant shoots and roots (Glick 1995, Kloepper et al. 2004, Kokalis-Burelle et al. 2006, Yildirim et al. 2006; van Loon, 2007). Humberto et al. (2010) showed that inoculation of tomato plants with growth promoting *Bacillus subtilis* led to tomato root growth promotion and this was evident 3 weeks after inoculation. These findings corroborate these results in which growth promotion of cotton roots was evident 2 weeks after inoculation. In addition to promoting root growth, PGPR-treated plants enhance a plant's ability to defend itself from insects and pathogens by eliciting defensive responses, also known as induced systemic resistance (ISR) (Kloepper et al. 2004) or by antibiosis (Zehnder et al. 2001). Some of the reported examples include reduced insect herbivory in cucumber *Cucumis saliva* (L.) (Zehnder et al. 1997) and resistance to whitefly *Bemicia tabaci* (Hanafi et al. 2007).

The results of the behavioral experiments clearly show the ability of the specialist parasitic wasp, *M. croceipes*, to detect, distinguish and exploit the differences between PGPR treated versus untreated plants. Specifically, PGPR treated plants were highly attractive to parasitoids, with Blend 9 treated plants being the most attractive. Further evaluation demonstrated that Blend 9-treated but uninfested plants were even more attractive to parasitoids than untreated plants with low levels of caterpillar infestations (2 *H. virescens* caterpillars per plant). Volatile organic compounds (VOCs) emitted systematically by plants can act as host location cues for foraging parasitoids (Röse et al. 1998, De Moraes et al. 1998, Ngumbi et al. 2009). These results showed that PGPR-treated plants were highly attractive to parasitoids as compared to untreated plants. These findings could be attributed to the blend of VOCs being produced by the PGPR-treated plants that is absent in the headspace of untreated plants. These PGPR-induced compounds have been implicated in natural enemy attraction through behavioral studies and antennal electrophysiological studies (Röse et al. 1998, Chen and Fadamiro 2007, Ngumbi et al. 2009). These data clearly showed the ability of the specialist parasitic wasp, *M. croceipes*, to detect, distinguish and exploit the differences between PGPR-treated versus untreated plants.

Among the tested PGPR treatments, Blend 9-treated plants were the most attractive to parasitoids. Interestingly, Blend 9-treated plants consistently did not release β-ocimene. Thus, the absence of 1-ocimene in the blend of VOCs emitted by Blend 9 treated plants might be responsible for the enhanced attraction of *M. croceipes* to PGPR Blend 9-treated plants. Previous studies have reported that parasitoids like *M. croceipes* can detect and exploit qualitative and quantitative differences in blends of VOCs when searching for their herbivore hosts (De Moraes et al. 1998). In a related study investigating the impact of PGPR on natural enemies of *Myzus persicae* (Hemiptera: Aphididae), Boutard-Hunt et al. (2009) reported that densities of natural enemies were significantly higher in plots treated with PGPR as compared to untreated plots. By providing specific and reliable chemical signals, plants may acquire a competitive advantage in the recruitment of herbivore natural enemies.

In summary, these results show that treatment of cotton plants with single strains or blends of several strains of PGPR (plant growth-promoting rhizobacteria) elicits changes in cotton plant VOCs with important consequences for foraging parasitoids. Together, the results suggest that PGPR treatment could signal low levels of caterpillar damage necessary for attraction of parasitoids to plants, most likely via increased emission of HIPVs. These findings establish a new function for PGPR in mediating insect-plant and tri-trophic interactions.

Further studies are needed to investigate if increased emission and induction of VOCs by PGPR is a common phenomenon in multiple crops under different ecological conditions. Additional studies are necessary to test if key natural enemy species in other cropping systems show similar response to PGPR-treated plants. If confirmed, results from such studies will demonstrate that treatment of plants with PGPR may be a viable component of integrated pest management of pests in many agro-ecosystems.

Example 2

Effects of PGPR on the Egg-Laving Behavior of Spodoptera Exigua

Abstract

Treating crops with plant growth-promoting rhizobacteria (PGPR) has been shown to increase plant growth and enhance plant health in a variety of ways. Previously, these bacteria have been studied in models using only one to two strains of PGPR, limiting our understanding of how different strains may interact. Furthermore, little is known about the potential effects of PGPR on plant insect interactions. To determine the effects of PGPR on the oviposition behavior of Spodoptera exigua on PGPR-treated cotton plants, an egg-laying choice study was performed. The total number of eggs and egg batches laid on cotton plants treated with PGPR versus untreated cotton plants were recorded. Here, Spodoptera exigua exhibited an egg-laying preference on untreated cotton plants versus PGPR-treated cotton plants. No eggs were recorded on one of the tested PGPR treatments comprising Bacillus amyloliquefaciens.

Materials and Results

Two experiments were conducted to test different PGPR blends/strains. In Experiment 1, cotton plant seeds were treated with 1 ml of three different aqueous spore seed preparations (Blend 8, Blend 9, and INR-7, see Example 1) at a concentration of $10^7$ cfu/ml. In Experiment 2, PGPR strains ABU 288 (Bacillus simplex) and MBI 600 (Bacillus subtilis) were tested. An untreated control was included for both Experiments.

Figure 9:
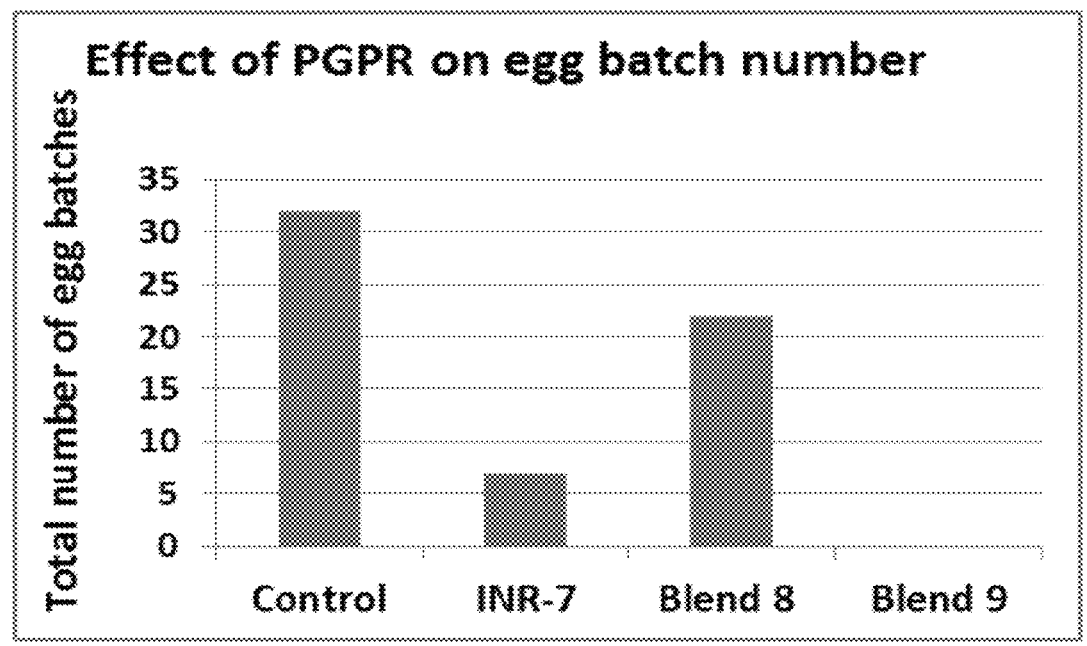
FIG. 9. Effect of PGPR on number of egg batches layed (A); and number of total eggs layed (B).
Figure 9:
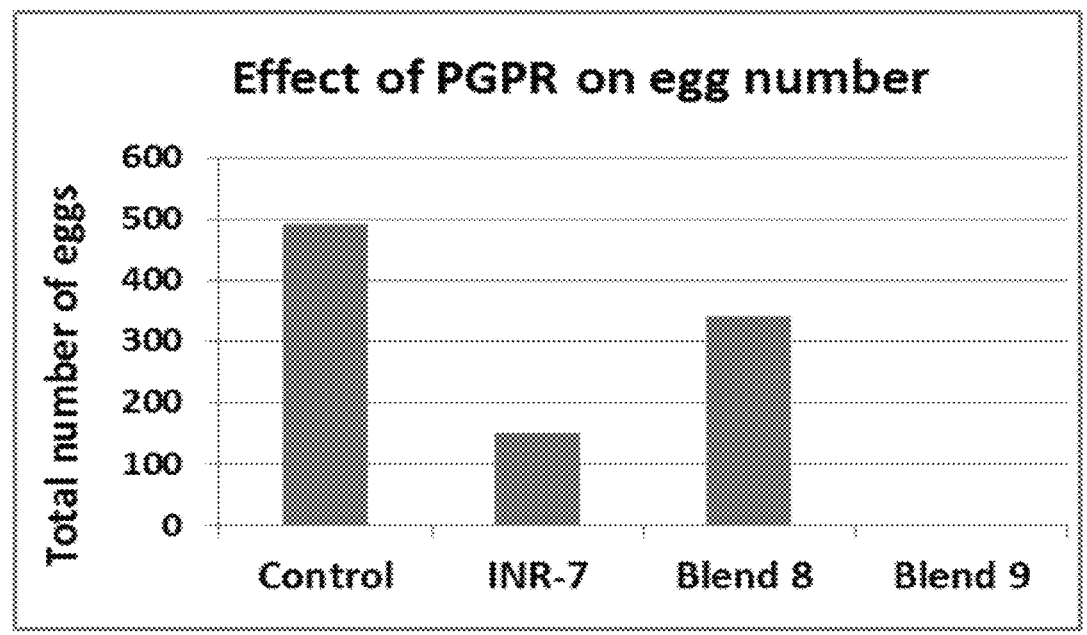

Female and male Spodoptera exigua were allowed to mate. Males were marked for separation later, and thirty mated females were separated from the males. For each of 8 replicates, 30 mated female Spodoptera exigua were caged overnight for a 14 hour period. The cage (42"×42"×32" tall) was placed in a dark room and each of the four corners had one cotton plant (4-5 weeks old) of each of the four treatments, respectively. Plant stems were placed 80 cm apart, and plants were rotated between replicates. After 14 hours, the number of egg masses and total number of eggs per plant were counted. Results are presented in Table 4 and FIG. 9 for Experiment 1, and in Table 5 for Experiment 2.

TABLE 4

Egg-laying of Spodoptera exigua on PGPR-treated (INR7, Blend 8 and Blend 9) versus untreated cotton plants

| Treatment | Total number of eggs laid | Total number of egg batches laid | Number of replicates during which treatment plant had eggs laid on it (out of 8) |
|---|---|---|---|
| Control | 491 | 32 | 8 |
| INR-7 | 151 | 7 | 4 |
| Blend 8 | 341 | 22 | 6 |
| Blend 9 | 0 | 0 | 0 |

TABLE 5

Egg-laying of Spodoptera exigua on PGPR-treated (strains MBI 600 or ABU 288) versus untreated cotton plants

| Treatment | Total number of eggs laid | Total number of egg batches laid |
|---|---|---|
| Control | 105 | 3 |
| MBI 600 | 0 | 0 |
| ABU 288 | 0 | 0 |

The results of both experiments illustrate a trend whereby Spodoptera exigua preferred to lay their eggs on untreated cotton plants versus PGPR-treated cotton plants. No eggs were laid on PGPR Blend 9 (Experiment 1) and strains MBI 600 and ABU 288 (Experiment 2).

Figure 10:
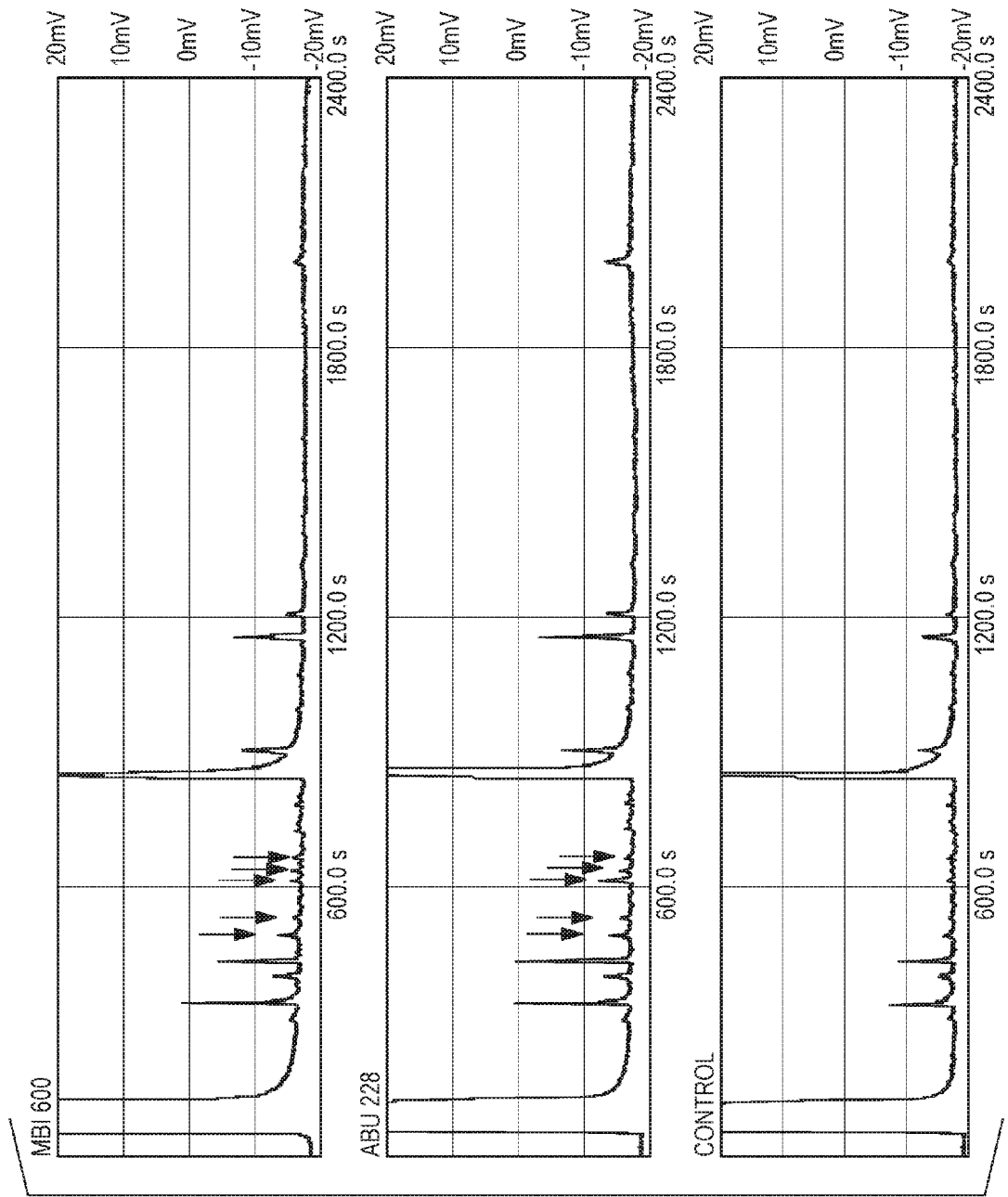
FIG. 10. Chromatographic profiles of headspace volatiles from untreated (control) cotton plants vs. cotton plants treated with PGPR strain MBI 600, or PGPR strain ABU 288. Arrows denote volatiles peaks detected in PGPR-treated plants but not in untreated (control) plants.

Headspace volatiles were collected for plants in Experiment 2. As for plants treated with Blend 8, Blend 9, and INR-7 (see Example 1, FIG. 1), induction of VOCs by plants treated with strains MBI 600 and ABU 288 versus control plants was observed (FIG. 10). Quantitative and qualitative differences in headspace volatiles collected from cotton treated with either strain compared to untreated cotton plants were observed. The peaks induced by strains MBI 600 and ABU 288 versus control likely are small molecular weight terpenoid compounds such as monoterpenes and sesquiterpenes.

REFERENCES

Alborn, H. T., T. C. J. Turlings, T. H. Jones, G. Stenhagen, J. H. Loughrin, and J. H. Tumlinson. 1997. An elicitor of plant volatiles from beet armyworm oral secretion. Science. 276: 945-949.

Ament, K., M. R. Kant, M. W. Sabelis, M. A. Haring, and R. C. Schuurink. 2004. Jasmonic acid is a key regulator of spider-mite induced volatile terpenoid and methyl salicylate emission in tomato. Plant Physiol. 135: 2025-2037.

Backman, P. A., M. Wilson, and J. F. Murphy. 1997. Bacteria for biological control of plant diseases. In. N. A Rechcigl and J. E. Rechcigl (eds.), pp. 95-109. Environmentally Safe Approaches to Crop Disease Control. Lewis Publishers, Boca Raton, Fla.

Banchio, E., X. Xie, H. Zhang, and P. W. Pare. 2009. Soil bacteria elevate essential oil accumulation and emission in sweet basil. J. Agric. Food Chem. 57: 653-657.

Boutard-Hunt, C., C. D. Smart, J. Thaler, and B. A. Nault. 2009. Impact of plant growth-promoting rhizobacteria and natural enemies of Myzus persicae (Hemiptera: Aphididae) infestations in pepper. J. Econ. Entomol. 102: 2183-2191.

Burkett-Cadena, M., N. Kokalis-Burelle, K. S. Lawrence, E. van Santen, and J. W. Kloepper. 2008. Suppressiveness of root-knot nematodes mediated by rhizobacteria. Biol. Cont. 47: 55-59.

Cardoza, Y. J., H. T. Albom, and J. H. Tumlinson. 2002. In vivo volatile emissions from peanut plants induced by simultaneous fungal infection and insect damage. J. Chem. Ecol. 28: 161-174.

Chen, L., and H. Y. Fadamiro. 2007. Differential electroantennogram response of females and males of two parasitoid species to host-related green leaf volatiles and inducible compounds. Bull. Entomol. Res. 97: 515-522.

Cleyet-Marcel, J. C., M. Larcher, H. Bertrand, S. Rapior, and X. Pinochet. 2001. Plant growth enhancement by rhizobacteria. In: J. F. Morot-Gaudry (ed.), pp. 185-197. Nitrogen Assimilation by Plants. Physiological, Biochemical and Molecular aspects. Science Publishers, Inc., Enfeld, N.H.

De Bruxelles, G. L., and M. R. Roberts. 2001. Signals regulating multiple responses to wounding and herbivores. Crit. Rev. Plant Sci. 20: 487-521.

De Moraes, C. M., W. J. Lewis, P. W. Pare, H. T. Alborn, and J. H. Tumlinson. 1998. Herbivore-infested plants selectively attract parasitoids. Nature (London). 393: 570-573.

Farmer, E. E., E. Almeras, and V. Krishnamurthy. 2003. Jasmonates and related oxylipins in plant responses to pathogenesis and herbivory. Curr. Opin. Plant Biol. 6: 372-378.

Glick, B. R. 1995. The enhancement of plant growth by free-living bacteria. Can. J. Microbiol. 41: 109-117.

Gouinguené, S. P., and T. C. J. Turlings. 2002. The effects of abiotic factors on induced volatile emissions in corn plants. Plant Physiol. 129: 1296-1307.

Gouinguené, S. P., J. A. Pickett, L. J. Wadhams, M. A. Birkett, and T. C. J. Turlings. 2005. Antennal electrophysiological responses of three parasitic wasps to caterpillar-induced volatiles from maize (*Zea mays mays*), cotton, (*Gossypium herbaceum*), and cowpea (*Vigna unguiculata*). J. Chem. Ecol. 31: 1023-1038.

Hanafi, A., M. Traore, W. H. Schnitzler, and M. Woitke. 2007. Induced resistance of tomato to whiteflies and Phytium with the PGPR *Bacillus subtilis* in a soilless crop grown under greenhouse conditions. In: A. Hanafi, and W. H. Schnitzler (eds.), pp. 315-322. Proceedings of VIIIth IS on protected cultivation in mild winter climates. Acta Horticul.

Humberto, J., V. Soto, M. G. Estrada-Hernández, E. Ibarra-Lacelette, and J. P Délano-Frier. 2010. Inoculation of tomato plants (*Solanum lycopersicum*) with growth-promoting *Bacillus subtilis* retards whitefly *Bemicia tabaci* development. Planta. 231: 397-410.

Jalali S. K., S. P. Singh, and C. R. Ballal. 1987. Studies on host age preference and biology of exotic parasite, *Cotesia marginiventris* (Cresson) (Hymenoptera: Braconidae). Entomon. 12: 59-62.

Ji, P., H. Campbell, J. W. Kloepper, J. Jones, T. Suslow, and M. Wilson. 2006. Integrated biological control of bacterial speck and spot of tomato under field conditions using foliar biological control agents and plant growth-promoting rhizobacteria. Biol. Control. 36: 358-367.

King, E. G., J. E. Powell, and R. J. Coleman. 1985. A high incidence of parasitism of *Heliothis* spp. (Lepidoptera: Noctuidae) larvae in cotton in southeastern Arkansas. Entomophaga. 30: 419-426.

Kloepper, J. W. 1992. Plant growth-promoting rhizobacteria as biological control agents. In. F, B. Metting Jr. (ed.), pp. 255-274. Soil Microbial Ecology: Applications in Agricultural and Environmental Management. Marcel Dekker Inc., New York.

Kloepper, J. W., R. Rodriguez-Kabana, G. W. Zehnder, J. Murphy, E. Sikora, and C. Fernandez. 1999. Plant root-bacterial interactions in biological control of soilborne diseases and potential extension to systemic and foliar diseases. Aust. J. Plant Pathol. 28: 27-33.

Kloepper, J. W., C. M. Ryu, and S. A Zhang. 2004. Induced systemic resistance and promotion of plant growth by *Bacillus* spp. Phytopathol. 94: 1259-1266.

Kloepper, J. W. and C. M. Ryu. 2006. Bacterial endophytes as elicitors of induced systemic resistance. In: B. Schulz, B. Boyle, and T. Siebern (eds.) Microbial root endophytes. Springer-Verlag, Heildelberg. pp. 33-51.

Kokalis-Burelle, N., C. S. Vavrina, M. S. Reddy, and J. W. Kloepper. 2003. Amendment of muskmelon and watermelon transplant media with plant growth-promoting rhizobacteria: effects on disease and nematode resistance. HortTechnology. 13: 476-482.

Kokalis-Burelle, N., J. W. Kloepper, and M. S. Reddy. 2006. Plant growth-promoting rhizobacteria as transplant amendments and their effects on indigenous rhizosphere microorganisms. Appl. Soil Ecol. 31: 91-100.

Lewis, W. J., and R. L. Burton. 1970. Rearing *Microplitis croceipes* in the laboratory with *Heliothis zea* as host. J. Econ. Entomol. 63: 656-658.

Loughrin, J. H., A. Manukian, R. R. Heath, and J. H. Tumlinson. 1994. Diurnal cycle emission of induced volatile terpenoids by herbivore-injured cotton plants. Proc. Natl. Acad. Sci. USA. 91: 11836-11840.

Lucy, M., E. Reed, and B. R. Glick. 2004. Applications of free living plant growth-promoting rhizobacteria. Antonie van Leeuwenhoek. 86: 1-25.

Mattiaci L., M. Dicke, and M. A. Posthumus. 1995. β-Glucosidase: An elicitor of herbivore-induced plant odor that attracts host searching parasitic wasps. Proc. Natl. Acad. Sci. USA. 92: 2036-2040.

Mithöfer, A., B. Schulze, and W. Boland. 2004. Biotic and heavy metal stress response in plants: evidence for common signals. FEBS Letters. 566: 1-5.

Mithöfer, A., G. Wanner, and W. Boland. 2005. Effects of feeding *Spodoptera littoralis* on lima bean leaves. II. Continuous mechanical wounding resembling insect feeding is sufficient to elicit herbivory-related volatile emission. Plant Physiol. 137: 1160-1168.

Ngumbi, E. N., L. Chen, and H. Y. Fadamiro. 2009. Comparative GC-EAD responses of a specialist (*Microplitis croceipes*) and a generalist (*Cotesia marginiventris*) parasitoid to cotton volatiles induced by two caterpillar species. J. Chem. Ecol. 35: 1009-1020.

Niranjan Raj, S., S. A. Deepak, P. Basavaraju, H. S. Shetty, M. S. Reddy, and J. W. Kloepper. 2003. Comparative performance of formulations of plant growth promoting rhizobacteria in growth promotion and suppression of downy mildew in pearl millet. Crop Protect. 22: 579-588.

Pieterse, C. M. J., S. C. M. Van Wees, E. Hoffland, J. A. Van Pelt, and L. C. Van Loon. 1996. Systemic resistance in *Arabidopsis* induced by biocontrol bacteria is independent of salicylic acid accumulation and pathogenesis-related gene expression. Plant Cell. 8: 1225-1237.

Preston, C. A., C. A. Lewandowski, J. Enyedi, and I. T. Baldwin. 1999. Tobacco mosaic virus inoculation inhibits wound-induced jasmonic acid mediated responses within but not between plants. Planta. 209: 87-95.

Ramamoorthy, V., R. Viswanathan, T. Raguchander, V. Prakasam, and R. Samiyappan. 2001. Induction of systemic resistance by plant growth-promoting rhizobacteria in crop plants against pests and diseases. Crop Prot. 20: 1-11.

Röse, U. S. R., W. J. Lewis, and J. H. Tumlinson. 1998. Specificity of systemically released cotton volatiles as attractants for specialist and generalist parasitic wasps. J. Chem. Ecol. 24: 303-319.

Ryu, C., M. A. Farag, C. Hu, M. S. Reddy, J. W. Kloepper, and P. W. Pare. 2004. Bacterial volatiles induce systemic resistance in *arabidopsis*. Plant Physiol. 134: 1017-1026.

SAS Institute. 2007. JMP® 7.0.1. Cary, N.C., USA.

Schippers, G., A. W. Baker, and P. A. H. M. Bakker. 1987. Interactions of deleterious and beneficial rhizosphere microorganisms and the effect on cropping practices. Annu. Review Phytopathol. 25: 339-358.

Shorey, H. H., and R. L. Hate. 1965. Mass rearing of the larvae of nine noctuid species on a simple artificial medium. J. Econ. Entomol. 58: 55-68.

Stadelbacher, E. A., J. E. Powell, and E. H. King. 1984. Parasitism of *Heliothis zea* and *Heliothis virescens* (Lepidoptera: Noctuidae) larvae in wild and cultivated host plants in the Delta of Mississippi. Environ. Entomol. 13: 1167-1172.

Takabayashi, J., M. Dicke, and M. A. Posthumus. 1994. Volatile herbivore-induced terpenoids in plant-mite interactions, variation caused by biotic and abiotic factors. J. Chem. Ecol. 20: 1329-1354.

Thaler, J. S., R. Karban, D. E. Ullman, K. Boege, and R. M. Bostock. 2002. Cross-talk between jasmonate and salicylate plant defense pathways: effects on several plant parasites. Oecologia. 131: 227-235.

Van Loon, L. C., P. A. H. M. Bakker, and C. M. J. Pierterse. 1998. Systemic resistance induced by rhizosphere bacteria. Annu. Rev. Phytopathol. 36: 453-483.

Yildrim, E., A. G. Taylor, and T. D. Spittler. 2006. Ameliorative effects of biological treatments on growth of squash plants under salt stress. Scientia Horticult. 111: 1-6.

Zehnder, G. W., J. W. Kloepper, T. Tuzun, C. Yao, G. Wei, O. Chambliss, and R. Shelby. 1997. Insect feeding on cucumber mediated rhizobacteria-induced plant resistance. Entomol. Exp. Appl. 83: 81-85.

Zehnder, G. W., J. F. Murphy, E. J. Sikora, and J. W. Kloepper. 2001. Application of Rhizobacteria for induced resistance. Eur. J. Plant Pathol. 107: 39-50.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A composition for treating a plant or seeds of a plant, the composition formulated as a treatment composition in which are combined:
   (a) an isolated *Bacillus* bacteria selected from the group consisting of:
      (i) *Bacillus amyloliquefaciens* selected from the group consisting of *Bacillus amyloliquefaciens* strain AP-136 (NRRL B-50614), *Bacillus amyloliquefaciens* strain AP-188 (NRRL B-50615), *Bacillus amyloliquefaciens* strain AP-218 (NRRL B-50618), *Bacillus amyloliquefaciens* strain AP-219 (NRRL B-50619), and *Bacillus amyloliquefaciens* strain AP-295 (NRRL B-50620);
      (ii) *Bacillus mojavensis* strain AP-209 (NRRL B-50616);
      (iii) *Bacillus solisalsi* strain AP-217 (NRRL B-50617);
      (iv) *Bacillus simplex* strain ABU 288 (NRRL B-50340); and
      (v) mixtures thereof; and
   (b) a suitable carrier;
   the composition comprising $10^2$-$10^{12}$ cfu per ml carrier, and the composition inducing production of one or more volatile organic compounds (VOCs) by a plant that has been treated with the composition or that is grown from seed that has been treated with the composition.

2. The composition according to claim 1, wherein the bacteria are selected from a group consisting of *Bacillus amyloliquefaciens* strain AP-136 (NRRL B-50614), *Bacillus amyloliquefaciens* strain AP-188 (NRRL B-50615), *Bacillus amyloliquefaciens* strain AP-218 (NRRL B-50618), *Bacillus*

*amyloliquefaciens* strain AP-219 (NRRL B-50619), and *Bacillus amyloliquefaciens* strain AP-295 (NRRL B-50620).

3. The composition according to claim 1, wherein the bacteria are *Bacillus mojavensis* strain AP-209 (NRRL B-50616).

4. The composition according to claim 1, wherein the bacteria are *Bacillus solisalsi* strain AP-217 (NRRL B-50617).

5. The composition according to claim 1, wherein the bacteria are *Bacillus simplex* strain ABU 288 (NRRL B-50340).

6. The composition according to claim 1, wherein the carrier is selected from the group consisting of peat, wheat, bran, vermiculite, and pasteurized soil.

7. The composition according to claim 1, wherein the one or more VOCs comprise one or more compounds selected from a group consisting of alpha-pinene, beta-pinene, beta-myrcene, cis-3-hexenyl acetate, limonene, beta-ocimene, linalool, (E)-4,8-dimethyl-1,3,7-nonatriene, methyl salicylate, decanal, cis-jasmone, caryophyllene, alpha-humulene, beta-farnesene, and mixtures thereof.

8. The composition according to claim 1, wherein one or more VOCs reduce egg-laying of an insect on the plant.

9. The composition according to claim 1, wherein one or more VOCs reduce feeding of an insect on the plant.

10. The composition according to claim 1, wherein one or more VOCs attract a predator or a parasitoid to the plant.

11. A method of treating a plant, the method comprising administering the composition of claim 1 to the plant or to soil surrounding the plant.

12. The method according to claim 11, wherein the plant is selected from the group consisting of alfalfa, rice, barley, rye, cotton, sunflower, peanut, corn, potato, sweet potato, bean, pea, lentil chicory, lettuce, endive, cabbage, brussel sprout, beet, parsnip, turnip, cauliflower, broccoli, turnip, radish, spinach, onion, garlic, eggplant pepper, celery, carrot, squash, pumpkin, zucchini, cucumber, apple, pear, melon, citrus, strawberry, grape, raspberry, pineapple, soybean, canola, oil seed rape, spring wheat, winter wheat, tobacco, tomato, sorghum, and sugarcane.

13. The method according to claim 11, wherein the method reduces egg-laying of an insect on the plant.

14. The method according to claim 11, wherein the method reduces feeding of an insect on the plant.

15. The method according to claim 11, wherein the method attracts a predator insect or parasitoid to the plant.

16. A method of treating a plant seed, the method comprising treating the plant seed with the composition of claim 1.

* * * * *

SEQUENCE LISTING

```
<160> NUMBER OF SEQ ID NOS: 6

<210> SEQ ID NO 1
<211> LENGTH: 1577
<212> TYPE: DNA
<213> ORGANISM: Bacillus amyloliquefaciens

<400> SEQUENCE: 1
gatcctggct caggacgaac gctggcggcg tgcctaatac atgcaagtcg agcggacaga      60
tgggagcttg ctccctgatg ttagcggcgg acgggtgagt aacacgtggg taacctgcct     120
gtaagactgg gataactccg ggaaaccggg gctaataccg gatggttgtc tgaaccgcat     180
ggttcagaca taaaggtgg cttcggctac cacttacaga tggacccgcg gcgcattagc     240
tagttggtga ggtaacggct caccaaggcg acgatgcgta gccgacctga gagggtgatc     300
ggccacactg ggactgagac acggcccaga ctcctacggg aggcagcagt agggaatctt     360
ccgcaatgga cgaaagtctg acggagcaac gccgcgtgag tgatgaaggt tttcggatcg     420
taaagctctg ttgttaggga agaacaagtg ccgttcaaat agggcggcac cttgacggta     480
cctaaccaga aagccacggc taactacgtg ccagagccgc gggtaatacg taggtggcaa     540
gcgttgtccg gaattattgg gcgtaaaggg ctcgcaagcg ttttcttaag tctgatgtga     600 aaccccggg ctcaaccggg gagggtcatt ggaaaccgag gaacttgagt gcagaagagg     660
agagtggaat tccacgtgta gcggtgaaat gcgtagagat gtggaggaac accagtggcg     720
aaggcgactc tctgttctgt aactgacgct gagagagcga agcgtgggga gcaacagaa     780 ttagataccc tggtagtcca cgccgtaaac gatgagtgct aagtgttagg gggtttccgc     840
cccttagtgc tgcagctaac gcattaagca ctccgcctgg ggagtacggt cgcaagactg     900
aaactcaaag gaattgacgg gggcccgcac aagcggtgga catgtggtt taattcgaag     960 caacgcgaag aaccttacca ggtcttgaca tcctctgaca atcctagaga taggacgtcc    1020
ccttcggggg cagagtgaca ggtggtgcat ggttgtcgtc agctcgtgtc gtgagatgtt    1080
gggttaagtc ccgcaacgag cgcaaccctt gatcttagtt gccagcattc agttgggcac    1140
```
tctaaggtga ctgccggtga caaaccggag gaaggtgggg atgacgtcaa atcatcatgc    1200
cccttatgac ctgggctaca cacgtgctac aatggacaga acaaagggca gcgaaaccgc    1260
gaggttaagc caatcccaca aatctgttct cagttcggat cgcagtctgc aactcgactg    1320
cgtgaagctg gaatcgctag taatcgcgga tcagcatgcc gcggtgaata cgttcccggg    1380
ccttgtacac accgcccgtc acaccacgag agtttgtaac acccgaagtc ggtgaggtaa    1440
cctttatgga gccagccgcc gaaggtggga cagatgattg gggtgaagtc gtaacaaggt    1500
agccgtatcg gaaggtgcgg ctggatcacc tcctttctaa ggattttaac ggaatataag    1560
accttgggtc ttataac                                                  1577

<210> SEQ ID NO 2
<211> LENGTH: 1485
<212> TYPE: DNA
<213> ORGANISM: Bacillus mojavensis

<400> SEQUENCE: 2
cgggtacgtc ttctagtttg atcctggctc agtgcggctg ggtagcttgc tccctgatgt      60
tagcggcgga cgggtgagta acacgtgggt aacctgcctg taagactggg ataactccgg     120
gaaaccgggg ctaataccgg atggttgttt gaaccgcatg gttcaaacat aaaaggtggc     180
ttcggctacc acttacagat ggacccgcgg cgcattagct agttggtgag gtaacggctc     240
accaaggcaa cgatgcgtag ccgacctgag agggtgatcg ccacactgg gactgagaca     300 cggcccagac tcctacggga ggcagcagta gggaatcttc cgcaatggac gaaagtctga     360
cggagcaacg ccgcgtgagt gatgaaggtt ttcggatcgt aaagctctgt tgttagggaa     420
gaacaagtac cgttcgaata gggcggtacc ttgacggtac ctaaccagaa agccccggct     480
aactacgtgc cagcagccgc ggtaatacgt aggtggcaag cgttgtccgg aattattggg     540
cgtaaagggc tcgcacgcgg tttcttaaat ctgatgtgaa agccccggc tcaaccgggg     600 agggtcattg gaaactgggg aacttgagtg cagaaaagga gagtggaatt ccacgtgtag     660
cggtgaaatg cgtagagatg tggaggaaca ccagtggcga aggcgactct ctggtctgta     720
actgacactg aggagcgaga gcgtggggag cgaacaggat tagataccct ggtagttccc     780
cccgtaaacg atgagtggta agtgttaggg ggtttccccc ccttagtggt gcaggtaacg     840
cattaagcac tccccctggg gagtacggtc gcaaggctga aactcaaagg aattgacggg     900
ggcccgcacc agcggtggag catgtggttt aatttgaagc aacgcgaaga accttaccag     960
gtcttgacat cctctgacaa tcctagagat aggacgtccc ctttgggggc agagtgacag    1020
gtggtgcatg gttgttgtca gctcgtgtcg tgagatgttg ggttaagtcc cgcaacgagc    1080
gcaacccttg atcttagttg ccagcattta gttgggcact taaggtgac tgccggtgac    1140 aaaccggagg aaggtgggga tgacgtcaaa tcatcatgcc ccttatgacc tgggctacac    1200
acgtgctaca atggacagaa caaagggcag cgaaaccgcg aggttaagcc aatcccacaa    1260
atctgttctc agttcggatc gcagtctgca actcgactgc gtgaagctgg aatcgctagt    1320
aatcgcggat cagcatgccg cggtgaatac gttcccgggc cttgtacaca ccgcccgtca    1380
caccacgaga gtttgtaaca cccgaagtcg gtgaggtaac cttttaggag ccagccgccg    1440
aaggtgggac agatgattgg gggaagacct aactagagga gtgcc                   1485

<210> SEQ ID NO 3
<211> LENGTH: 1424
<212> TYPE: DNA

<213> ORGANISM: Bacillus solisalsi

<400> SEQUENCE: 3

| | | | | | |
|---|---|---|---|---|---|
| tacatgcaag | tcgagcggac | agatgaggag | cttgctcctc | tgatgttagc | ggcggacggg | 60 |
| tgagtaacac | gtgggcaacc | tacctgtaag | acggggataa | ctccgggaaa | ccggagctaa | 120 |
| taccggataa | taaagagaaa | cgcctgtttc | tttttgaaa | gtcggtttcg | gctgacactt | 180 |
| acagatgggc | ccgcggcgca | ttagctagtt | ggtgaggtaa | cggctcacca | aggcgacgat | 240 |
| gcgtagccga | cctgagaggg | tgatcggcca | cactgggact | gagacacggc | ccagactcct | 300 |
| acggaggca | gcagtaggga | atcttcggca | atggacgaaa | gtctgaccga | gcaacgccgc | 360 |
| gtgagcgatg | aaggccttcg | ggtcgtaaag | ctctgttgtc | agggaagaac | aagtaccgga | 420 |
| gtaactgccg | gtaccttgac | ggtacctgac | cagaaagcca | cggctaacta | cgtgccagca | 480 |
| gccgcggtaa | tacgtaggtg | gcaagcgttg | tccggaatta | ttgggcgtaa | agcgcgcgca | 540 |
| ggcggttctt | taagtctgat | gtgaaagccc | acggctcaac | cgtggagggt | cattggaaac | 600 |
| tggggaactt | gagtgcagga | gagaaaagtg | gaattccacg | tgtagcggtg | aaatgcgtag | 660 |
| agatggggag | gaaccccagt | ggcgaaggcg | gcttttttggc | ctgtaactga | cgctgaggcg | 720 |
| cgaaagcgtg | gggagcaaac | aggattagat | accctggtag | tccacgccgt | aaacgatgag | 780 |
| tgctaggtgt | tgggggggtt | ccaccctcag | tgctgacgtt | aacacattaa | gcactccgcc | 840 |
| tggggagtac | gggccgcaag | gctgaaactc | aaaaggaatt | gacgggggcc | cgcacaagca | 900 |
| gtggagcatg | tggtttaatt | cgaagcaacg | cgaagaacct | taccaggtct | tgacatcctc | 960 |
| tgaccacttg | agagatcaag | ctttccccctt | cgggggacag | agtgacaggt | ggtgcatggt | 1020 |
| tgtcgtcagc | tcgtgtcgtg | agatgttggg | ttaagtcccg | caacgagcgc | aacccttgac | 1080 |
| cttagttgcc | agcattcagt | tgggcactct | aaggtgactg | ccggtgacaa | accggaggaa | 1140 |
| ggtggggatg | acgtcaaatc | atcatgcccc | ttatgacctg | ggctacacac | gtgctacaat | 1200 |
| gggtggtaca | aagggttgcg | aagccgcgag | gccgagccaa | tcccaaaaag | ccactctcag | 1260 |
| ttcggattgt | aggctgcaac | tcgcctacat | gaagccggaa | ttgctagtaa | tcgcggatca | 1320 |
| gcatgccgcg | gtgaatacgt | tcccgggcct | tgtacacacc | gcccgtcaca | ccacgagagt | 1380 |
| ttgtaacacc | cgaagtcggt | ggggtaaccg | ttggagccag | ccgc | | 1424 |

<210> SEQ ID NO 4
<211> LENGTH: 1346
<212> TYPE: DNA
<213> ORGANISM: Bacillus pumilus

<400> SEQUENCE: 4

| | | | | | |
|---|---|---|---|---|---|
| tacatgcaag | tcgagtggac | agaagggagc | ttgctcccgg | atgttagcgg | cggacgggtg | 60 |
| agtaacacgt | gggtaacctg | cctgtaagac | tgggataact | ccgggaaacc | ggagctaata | 120 |
| ccggatagtt | ccttgaaccg | catggttcaa | ggatgaaaga | cggtttcggc | tgtcacttac | 180 |
| agatggaccc | gcggcgcatt | agctagttgg | tggggtaatg | gctcaccaag | gcgacaatgc | 240 |
| gtagccaacc | tgagagggtg | atcggccaca | ctgggactga | acacggccc | aaactcctac | 300 |
| gggaggcacc | agtagggaat | cttccgcaat | ggacgaaagt | ctgacggagc | aacgccgcgt | 360 |
| gagtgatgaa | ggttttcgga | tcgtaaagct | ctgttgttag | ggatgaacaa | gtgcgagagt | 420 |
| aactgctcgc | accttgacgg | tacctaacca | gaaagccacg | gctaactacg | tgccagcacc | 480 |
| cgcggtaata | cgtaggtggc | aagcgttgtc | cggaattatt | gggcgtaaag | ggctcgcagg | 540 |
| cggtttctta | agtctgatgt | gaaagccccc | ggctcaaccg | ggagggtca | ttggaaactg | 600 |

```
ggaaacttga gtgcagaaga ggagagtgga attccacgtg tagcggtgaa atgcgtagag      660
atgtggagga acaccagtgg cgaaggcgac tctctggtct gtaactgacg ctgaggagcg      720
aaagcgtggg gagcgaacag gattagatac cctggtagtc cacgccgtaa acgatgagtg     780
ctaagtgtta gggggtttcc gcccttagt gctgcagcta acgcattaag cactccgcct      840
ggggagtacg gtcgcaagac tgaaactcaa aggaattgac ggggccccgc acaagcggtg     900
gagcatgtgg tttaattcga agcaacgcga agaaccttac caggtcttga catcctctga     960
caaccctaga gatagggctt tcccttcggg gacagagtga caggtggtgc atggttgtcg    1020
tcagctcgtg tcgtgagatg ttgggttaag tctcgcaacg agcgcaaccc ttgatcttag    1080
ttgccagcat tcagttgggc actctaaggt gactgccggt gacaaaccgg aggaaggtgg    1140
ggatgacgtc aaatcatcat gccccttatg acctgggcta cacacgtgct acaatggaca    1200
gaacaaagtg ctgcgagacc gcaaggttta gccaatccca taaatctgtt ctcagttcgg    1260
atcgcagtct gcaactcgac tgcgtgaagc tggaatcgct agtaatcgcg gatcagcatg    1320
ccgcggtgaa tacgttcccg ggcctt                                         1346

<210> SEQ ID NO 5
<211> LENGTH: 1529
<212> TYPE: DNA
<213> ORGANISM: Bacillus simplex

<400> SEQUENCE: 5
cgggatccga gtttgatcct ggtcagaacg aacgctggcg gcgtgcctaa tacatgcaag      60
tcgagcgaat cgatgggagc ttgctccctg agattagcgg cggacgggtg agtaacacgt     120
gggcaacctg cctataagac tgggataact tcgggaaacc ggggctaata ccggatacgt     180
tcttttctcg catgagagaa gatggaaaga cggtttacgc tgtcacttat agatgggccc     240
gcggcgcatt agctagttgg tgaggtaatg gctcaccaag gcgacgatgc gtagccgacc     300 tgaggggtg atcggccaca ctgggactga gacacgccc agactcctac gggaggcagc      360
agtagggaat cttccgcaat ggacgaaagt ctgacggagc aacgccgcgt gaacgaagaa     420
ggccttcggg tcgtaaagtt ctgttgttag gaagaacaa gtaccagagt aactgctggt      480
accttgacgg tacctaacca gaaagccacg gctaactacg tgccagcagc cgcggtaata     540
cgtaggtggc aagcgttgtc cggaattatt gggcgtaaag cgcgcgcagg tggttcctta    600
agtctgatgt gaaagcccac ggctcaaccg tggagggtca ttggaaactg ggaacttga    660 gtgcagaaga ggaaagtgga attccaagtg tagcggtgaa atgcgtagag atttggagga    720
acaccagtgg cgaaggcgac tttctggtct gtaactgaca ctgaggcgcg aaagcgtggg    780
gagcaaacag gattagatac cctggtagtc cacgccgtaa acgatgagtg ctaagtgtta    840
gagggtttcc gccctttagt gctgcagcta acgcattaag cactccgcct ggggagtacg    900
gccgcaaggc tgaaactcaa aggaattgac ggggcccgc acaagcggtg gagcatgtgg    960
tttaattcga agcaacgcga agaaccttac caggtcttga catcctctga caaccctaga   1020
gatagggctt tccccttcgg gggacagagt gacaggtggt gcatggttgt cgtcagctcg    1080
tgtcgtgaga tgttgggtta agtcccgcaa cgagcgcaac ccttgatctt agttgccagc    1140
attcagttgg gcactctaag gtgactgccg gtgacaaacc ggaggaaggt ggggatgacg    1200
```

-continued

```
tcaaatcatc atgccccta tgacctgggc tacacacgtg ctacaatgga tggtacaaag    1260
ggctgcaaac ctgcgaaggt aagcgaatcc cataaagcca ttctcagttc ggattgcagg   1320
ctgcaactcg cctgcatgaa gccggaatcg ctagtaatcg cggatcagca tgccgcggtg   1380
aatacgttcc cgggccttgt acacaccgcc cgtcacacca cgagagtttg taacacccga   1440
agtcggtgag gtaaccttca tggagccagc cgcctaaggt gggacagatg attggggtga   1500
agtcgtaaca aggtagccgt aggatcccg                                    1529

<210> SEQ ID NO 6
<211> LENGTH: 1124
<212> TYPE: DNA
<213> ORGANISM: Bacillus subtilis

<400> SEQUENCE: 6
tgctatacat gcaagtcgag cggacagatg ggagcttgct ccctgatgtt agcggcggac     60
gggtgagtaa cacgtgggta acctgcctgt aagactggga taactccggg aaaccggggc    120
taataccgga tggttgtttg aaccgcatgg ttcagacata aaaggtggct tcggctacca    180
cttacagatg gacccgcggc gcattagcta gttggtgagg taacggctca ccaaggcgac    240
gatgcgtagc cgacctgaga gggtgatcgg ccacactggg actgagacac ggcccagact    300
cctacgggag gcagcagtag ggaatcttcc gcaatggacg aaagtctgac ggagcaacgc    360
cgcgtgagtg atgaaggttt tcggatcgta aagctctgtt gttagggaag aacaagtgcc    420
gttcaaatag ggcggcacct tgacggtacc taaccagaaa gccacggcta actacgtgcc    480
agcagccgcg gtaatacgta ggtggcaagc gttgtccgga attattgggc gtaaagggct    540
cgcaggcggt ttcttaagtc tgatgtgaaa gcccccggct caaccgggga gggtcattgg    600
aaactgggga acttgagtgc agaagaggag agtggaattc cacgtgtagc ggtgaaatgc    660
gtagagatgt ggaggaacac cagtggcgaa ggcgactctc tggtctgtaa ctgacgctga    720
ggagcgaaag cgtggggagc gaacaggatt agataccctg gtagtccacg ccgtaaacga    780
tgagtgctaa gtgttagggg gtttccgccc cttagtgctg cagctaacgc attaagcact    840
ccgcctgggg agtacggtcg caagactgaa actcaaagga attgacgggg gcccgcacaa    900
gcggtggagc atgtggttta attcgaagca acgcgagaac cttaccaggt cttgacatcc    960
tctgacatcc tagagatagg acgtcccctt cgggggcaga gtgacagtgg tgcatggttg   1020
tcgtcagctc gtgtcgtgag atgttgggta agtcccgcac gagcgcaccc ttgatcttag   1080
ttgccagcat tcagttggca ctctaaggtg actgccggtg acga                   1124
```